United States Patent
Wallner et al.

(10) Patent No.: US 6,770,628 B2
(45) Date of Patent: *Aug. 3, 2004

(54) HEMATOPOIETIC STIMULATION

(75) Inventors: Barbara P. Wallner, Weston, MA (US); Barry Jones, Cambridge, MA (US); Glenn T. Miller, Haverhill, MA (US); Sharlene Adams, Watertown, MA (US)

(73) Assignee: Point Therapeutics, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/878,792

(22) Filed: Jun. 11, 2001

(65) Prior Publication Data

US 2002/0013279 A1 Jan. 31, 2002

Related U.S. Application Data

(62) Division of application No. 09/304,199, filed on May 3, 1999, now Pat. No. 6,300,314.
(60) Provisional application No. 60/084,128, filed on May 4, 1998.

(51) Int. Cl.[7] .................. A61K 38/04; A61K 38/05; A61K 38/16
(52) U.S. Cl. ................ 514/19; 514/13; 514/14; 514/15; 514/16; 514/17; 514/18; 514/423
(58) Field of Search .................. 514/13, 14, 15, 514/16, 17, 18, 19, 20, 423; 435/70.3, 70.4, 70.5, 372, 372.1, 372.2, 372.3, 405, 406

(56) References Cited

U.S. PATENT DOCUMENTS

| 4,318,904 A | 3/1982 | Shaw et al. ............. 424/177 |
| 4,443,609 A | 4/1984 | Oude Alink et al. ....... 548/111 |

(List continued on next page.)

FOREIGN PATENT DOCUMENTS

| DD | 158109 | 12/1982 |
| DD | 270382 A1 | 7/1989 |

(List continued on next page.)

OTHER PUBLICATIONS

Colowick, S., et al., "Methods in Enzymology", pp. 220–225, vol. XLVI, (Not dated).

(List continued on next page.)

*Primary Examiner*—Jeffrey E. Russel
(74) *Attorney, Agent, or Firm*—Wolf, Greenfield and Sacks, P.C.

(57) ABSTRACT

Methods and products for stimulating hematopoiesis, preventing low levels of hematopoietic cells and producing increased numbers of hematopoietic and mature blood cells are provided. The methods and products can be used both in vivo and in vitro. The methods involve administering an agent of Formula I:

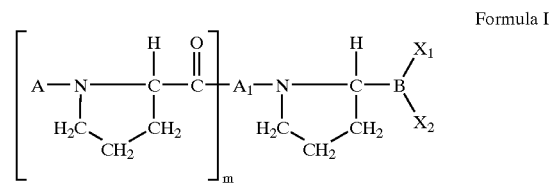

Formula I wherein m is an integer between 0 and 10, inclusive; A and $A_1$ are L-amino acid residues such that the A in each repeating bracketed unit can be the same or a different amino acid residue; the C bonded to B is in the L-configuration; the bonds between A and N, $A_1$ and C, and between $A_1$ and N are peptide bonds; and each $X_1$ and $X_2$ is, independently, a hydroxyl group or a group capable of being hydrolyzed to a hydroxyl group in aqueous solution at physiological pH. A particularly preferred agent that is useful in practicing the invention is a ValBoroPro.

21 Claims, 6 Drawing Sheets

U.S. PATENT DOCUMENTS

| | | | |
|---|---|---|---|
| 4,499,082 A | 2/1985 | Shenvi et al. | 514/2 |
| 4,582,821 A | 4/1986 | Kettner et al. | 514/18 |
| 4,636,492 A | 1/1987 | Kettner et al. | 514/18 |
| 4,644,055 A | 2/1987 | Kettner et al. | 530/330 |
| 4,652,552 A | 3/1987 | Kettner et al. | 514/18 |
| 4,935,493 A | 6/1990 | Bachovchin et al. | 530/331 |
| 4,963,655 A | 10/1990 | Kinder et al. | 530/331 |
| 5,093,477 A | 3/1992 | Mölling et al. | 530/328 |
| 5,187,157 A | 2/1993 | Kettner et al. | 514/18 |
| 5,215,926 A | 6/1993 | Etchells, III et al. | 436/501 |
| 5,242,904 A | 9/1993 | Kettner et al. | 514/18 |
| 5,250,720 A | 10/1993 | Kettner et al. | 558/288 |
| 5,288,707 A | 2/1994 | Metternich | 514/19 |
| 5,296,604 A | 3/1994 | Hanko et al. | 546/169 |
| 5,329,028 A | 7/1994 | Ashkenzi et al. | 548/548 |
| 5,378,624 A | 1/1995 | Berenson et al. | 435/239 |
| 5,384,410 A | 1/1995 | Kettner | 548/405 |
| 5,444,049 A | 8/1995 | de Nanteuil et al. | 514/18 |
| 5,462,928 A | 10/1995 | Bachovchin et al. | 514/19 |
| 5,506,130 A | 4/1996 | Peterson et al. | 435/240.1 |
| 5,527,923 A | 6/1996 | Klingler et al. | 548/570 |
| 5,543,396 A | 8/1996 | Powers et al. | 514/19 |
| 5,554,728 A | 9/1996 | Basava et al. | 530/327 |
| 5,635,386 A | 6/1997 | Palsson et al. | 435/372 |
| 5,635,387 A | 6/1997 | Fei et al. | 435/378 |
| 5,646,043 A | 7/1997 | Emerson et al. | 435/373 |
| 6,040,145 A * | 3/2000 | Huber et al. | 435/7.2 |
| 6,100,234 A * | 8/2000 | Huber et al. | 514/2 |
| 6,258,597 B1 | 7/2001 | Bachovchin et al. | 435/325 |
| 6,300,314 B1 * | 10/2001 | Wallner et al. | 514/19 |

FOREIGN PATENT DOCUMENTS

| | | |
|---|---|---|
| DD | 296075 A5 | 11/1991 |
| EP | 0356223 A2 | 2/1990 |
| EP | 0371467 A2 | 6/1990 |
| EP | 0471651 A2 | 2/1992 |
| EP | 0481311 A2 | 4/1992 |
| EP | 0615978 A1 | 9/1994 |
| EP | 0420913 B1 | 11/1995 |
| EP | 0688788 A1 | 12/1995 |
| WO | WO 89/03223 | 4/1989 |
| WO | WO 91/16339 | 10/1991 |
| WO | WO 91/17767 | 11/1991 |
| WO | WO 92/12140 | 7/1992 |
| WO | WO 92/17490 | 10/1992 |
| WO | WO 93/02057 | 2/1993 |
| WO | WO 93/05011 | 3/1993 |
| WO | WO 93/08259 | 4/1993 |
| WO | WO 93/10127 | 5/1993 |
| WO | WO 93/16102 | 8/1993 |
| WO | WO 94/03055 | 2/1994 |
| WO | WO 94/09132 | 4/1994 |
| WO | WO 94/20526 | 9/1994 |
| WO | WO 94/25873 | 11/1994 |
| WO | WO 94/28915 | 12/1994 |
| WO | WO 94/29335 | 12/1994 |
| WO | WO 95/11689 | 5/1995 |
| WO | WO 95/12618 | 5/1995 |
| WO | WO 95/15309 | 6/1995 |
| WO | WO 95/29190 | 11/1995 |
| WO | WO 95/29691 | 11/1995 |
| WO | WO 95/34538 | 12/1995 |
| WO | WO 96/40263 | 12/1996 |
| WO | WO 96/40858 | 12/1996 |
| WO | WO 98/00439 | 1/1998 |
| WO | WO 98/50046 | 11/1998 |
| WO | WO 98/50066 | 11/1998 |
| WO | WO 99/16864 | 4/1999 |

OTHER PUBLICATIONS

Cordes, E., et al., "Transition States for Hydrolysis of Acetals, Ketals Glycosides, and Glycosylamines", Chapter 11, pp. 429–465, (Not dated).

Thompson, R., "Use of Peptide Aldehydes to Generate Transition–State Analogs of Elastase", *Biochemistry*, (1973), 12:1:47–51.

Baugh, R., et al., "Proteinase and Tumor Invasion", (1980), 165:157–179.

Bodanszky, M., "Principles of Peptide Synthesis", Springer–Verlag, (1984), vol. 16.

Bodanszky, M., "The Practice of Peptide Synthesis", Springer–Verlag, (1984), vol. 21.

Matteson, D., et al., "Synthesis and Properties of Pinanediol—AM IDO Boronic Esters" *Organometallics*, (1984), 3:1284–1288.

Powers, C., et al., "Elastase Inhibitors for Treatment of Emphysema—NHLBI Workshop Summary", *U.S. Dept. of Health and Human Services*, (1985), 1097–1100.

Yoshimoti, T., et al., "Comparison of Inhibitory Effects of Prolinal–Containing Peptide Derivatives on Prolyl . . . ", (1985), 98:975–979.

Kettner, C.A., et al., "Kinetic Properties of the Binding of Alpha–Lytic Protease to Peptide Boronic Acids", *Biochemistry*, (1988), 27:7682–7688.

Tam, J.P., "Synthetic Peptide Vaccine Design: Synthesis and Properties of a High–Density Multiple Antigenic Peptide System", *Proc Natl Acad Sci U S A*, (1988), 85:5409–5413.

Bailey, P.D., "An Introduction to Pepetide Chemistry", *Wiley Publishers*, (1990), 1–81.

Kettner, C.A. and Shenvi, A.B., "Peptide Boronic Acid Inhibitors of Trypsin–Like Proteases, Their Preparation and Use as Coagulants and Inflammation Inhibitors", *Chemical Abstract Onlys*, (1990), 112:80 (91790c).

Bachovchin, W.W., et al., "Inhibition of IGA1 Proteinase from *Neisseria Gonorrhoeae* and *Hemophilus Influenzae* by Peptide Prolyl Boronic Acids", *J. Biol. Chem*, (1990), 265: 3738–3743.

Kinder D.H., et al., "Analogues of Carbamyl Aspartate as Inhibitors of Dihydroorotase Preparation of Boronic Acid Transition–State Analogues and a Zinc Chelator Carbamyl-homocysteine", Carbamylhomocysteine, *J. Med. Chem*, (1990), 33:819–823.

Flentke, G.R., et al., "Inhibition of Dipeptidyl Aminopeptidase IV (DP–IV) by XAA–Boropro Dipeptides and Use of These Inhibitors to Examine the Role of DP–IV in T–Cell Function", *Proc Natl Acad Sci U S A*, (1991), 88:1556–1559.

Schon, E., et al., "Dipeptidyl Peptidase IV in the Immune System", *Biol Chem* Hoppe–Seyler, (1991), 372:305–311.

Kubota, T., et al., "Involvement of Dipeptidyl Peptidase IV in an in Vivo Immune Response", *Clin Exp Immunol*, (1992), 89:192–197.

Kelly, T.A., et al., "Immunosuppressive Boronic Acid Dipeptides: Correlation Between Conformation and Activity", *J Am Chem Soc*, (1993), 115:12637–12638.

Songyang, Z., et al., "SH2 Domains Recognize Specific Phosphopeptide Sequences", *Cell*, (1993), 72:767–778.

Subramanyam, M., et al., "Mechanism of HIV–1 TAT Induced Inhibition of Antigen–Specific T Cell Responsiveness", *J Immunol*, (1993), 150:2544–2553.

Demuth, H.U. et al., "Design of (Omega–N–(O–ACYL)Hydroxy AMID) Aminodicarboxylic Acid Pyrrolidides as Potent Inhibitors of Proline–Specific Peptidases", *FEBS Lett*, (1993), 320:23–27.

Janeway, C., et al., "Immunobiology—The Immune System in Health and Disease", *Current Biology LTD,* (1994), Chapter 12, pp. 1–35.

Brady, L., and Dodson, G., "Reflections on a Peptide", *Nature,* (1994), 368:692–693.

Nicola, N, et al., "Guidebook to Cytokines and Their Receptors", Sambrook and Tooze Publication, (1994), pp. 1–257.

Perstorp Biotec Company, "Molecular Biology Catalog", (1994).

Jameson, B.A., et al., "A Rationally Designed CD4 Analogue Inhibits Experimental Allergic Encephalomyelitis", *Nature,* (1994), 368:744–746—Abstract Only.

Mosmann, T.R., "Cytokine Patterns During the Progression to Aids", *Science,* (1994), 265:193–194.

Seed, B., "Making Agonists of Antagonists", *Chemistry & Biology,* (1994), 1:125–129.

Austin, D.J., et al., "Proximity Versus Allostery: The Role of Regulated Protein Dimerization in Biology", *Chemistry & Biology,* (1994), 1:131–136.

Sudmeier, J.L., et al., "Solutions Structures of Active and Inactive Forms of the DP IV (CD26) Inhibitor Pro–Boropro Determined by NMR Spectroscopy", *Biochemistry,* (1994), 33:12427–12438.

Kubota, T., et al., "Dipeptidyl Peptidase (DP IV) Activity in Serum and on Lymphocytes of MRL–/Mp–lpr/lpr Mice Correlates with Disease Onset", *Clin Exp Immunol,* (1994), 96:292–296.

Snow, R.J., et al., "Studies on Proline Boronic Acid Dipeptide Inhibitors of Dipeptidyl Peptidase IV: Identification of a Cyclic Species Containing a B–N Bond", *J. Am. Chem. Soc,* (1994), 116:10860–10869.

Günther, U.L., et al., "Solution Structures of the DP IV (CD26) Inhibitor Val–BoroPro Determined by NMR Spectroscopy", Magnetic Resonance in Chem, (1995), 33:959–970.

Subramanyam, M., et al., "CD26, AT–Cell Accessory Molecule Induction of Antigen–Specific Immune–Suppression by Inactivation of CD26: A Clue to the AIDS Paradox?", in *Dipeptidyl Peptidase IV(CD26) in Metabolism and Immune Response,* (1995), Ed. B. Fleischer: 155–162.

Schmitz T, et al., "Potentiation of the Immune Response in HIV–1+Individuals", *J Clin Invest,* (1996), 97:1545–1549.

Aguila, H.L., et al., "From Stem Cells to Lymphocytes: Biology and Transplantation", *Immun Rev,* (1997), 157:13–40.

Dupont, B., "Immunology of Hematopoietic Stem Cell Transplantation: A Brief Review of its History", *Immun Rev,* (1997), 157:5–12.

Bodansky, M., "Peptide Chemistry, A Practical Textbook", Springer–Verlag, (1988) 1–9.

Boros, L.G., et al., "Fluoroolefin Peptide Isosteres—Tools for Controlling Peptide Conformations", *Tetrahedron Letters,* (1994), 35:6033–6036.

Goodman, M., and Chorev, M., "On the Concept of Linear Modified Retro–Peptide Structures", *Accounts of Chemical Research,* (1979), 12:1–7.

Guichard, G., et al., Partially Modified Retro–Inverso Pseudopeptides as Non–Natural Ligands for the Human Class 1 Histocompatibility Molecule HLA–A2, *J Med Chem,* (1996), 39:2030–2039.

Jardetzky, T.S., et al., Three–Dimensional Structure of a Human Class II Histocompatibility Molecule Complexed with Superantigen, *Nature,* (1994), 368:711–718.

Zimmerman, D.H., et al.,"A New Approach to T–Cell Activation: Natural and Synthetic Conjugates Capable of Activating T Cells", *Vaccine Res,* (1996), 5:91–102.

Zimmerman, D.H., et al., "Immunization with Peptide Heteroconjugates Primes A T Helper Cell . . . " *Vaccine Res,* (1996), 5:103–118.

Welch, J.T., and Lin J., Fluoroolefin Containing Dipeptide Isoteres as Inhibitors of Dipeptidyl Peptidase IV (CD26), *Tetrahedron,* (1995), 52:291–304.

Duke–Cohan, J.S., et al., "Targeting of an Activated T–Cell Subset Using a Bispecific Antibody–Toxin ConjugateDirected Against CD4 and CD26", *Blood,* (1993), 82:2224–2234. (Abstract only) directed against CD4 and CD26. Blood. Oct. 1, 1993; 82(7):2224–2234.

Kameoka, J., et al., "Direct Association of Adenosine Deaminase with a T Cell Activation Antigen, CD26", *Science,* (1993), 261:466–469. (Abstract only).

Hegen, M., et al., "Function of Dipeptidyl Peptidase IV (CD26, TP103) in Transfected Human T Cells", *Cell Immunol,* (1993), 146:249–260. (Abstract only).

Hegen, M., et al., "Enzymatic Activity of CD26 (DipeptidylPeptidase IV) is not Required for its Signalling Function in T Cells",*Jmmunobiology,* (1993), 189:483–493. (Abstract only).

Tanaka, T., et al., "The Costimulatory Activity of the CD26 Antigen Requires Dipeptidyl Peptidase IV Enzymatic Activity", *Proc Natl Acad Sci U S A,* (1993), 90:4586–4590. (Abstract only).

Tanaka, T., et al., "Cloning and Functional Expression of the T Cell Activation Antigen CD26", *J Immunol,* (1992), 149:481–486 (Abstract only).

Scharpe, S., et al., "Purified and Cell–Bound CD26: Enzymatic Inhibition, Antibody Binding Profile, and Expression on T Cells in Relation to Other Markers", *Verh K Acad Geneeskd Belg,* (1994), 56:537–559. (Abstract only).

Kameoka J., et al., "Differential CD26–Mediated Activation of the CD3 and CD2 Pathways After CD6–Depleted Allogeneic Bone Marrow Transplantation", *Blood,* (1995), 85:1132–1137. (Abstract only).

Mittrucker, H.W., et al., "The Cytoplasmic Tail of the T Cell Receptor ZETA Chain is Required for Signaling Via CD26", *Eur J Immunol,* (1995), 25:295–297. (Abstract only).

Morimoto, C., et al., 1F7 "A Novel Cell Surface Molecule, Involved In Helper Function Of CD4 cells", *J. Of Im* Morimoto,m I *Immunol.* 143:34030–3439 (1989) and published erratum appears in *J. Immunology* 144 (5):2027 (Mar. 1990). Abstract only.

Barton, R. W.J., et al., "Binding Of The T Cell Activation Monoclonal Ta1 to Dipeptidyl Peptidase IV", *Leukocyte Biology* 48:291–296 (1990). Abstract *J. Of Leukocyte Biology* 48:291–296 (1990). (Abstract only).

Bristol, L.A., et al., "Thymocyte Costimulating Antigen Is CD26 (Dipeptidyl–Peptidase IV), Co–stimulation Of Granulocyte, Macrophage, T Lineage Cell Proliferation Via CD26," *J. Of Immunol.* 149:367–372 (1992). Abstract only.

Bristol, L.A., et al.,"Characterization Of A Novel Rat Thymocyte Costimulating Antigen By The Monoclonal Antibody 1.3", *J. Of Immunol.* 148:332–338 (1992). Abstract Only).

Fleisher, B., et al., "Triggering Of Cytotoxic T Lymphocytes And NK Cells Via The Tp103 Pathway Is FIFF Dependent On the Expression Of The T Cell Receptor/CD3 Complex", *J. Of Immunol.* 141:1103–1107 Abstract Only.

Hegen, M., et al, "The T Cell Triggering Molecule bx;1Tp103 . . . " *J. Immunol.* 144:2980–2914 (1990). Abstract only.

Darmoul, D., et al., "Dipeptidyl Peptidase IV (CD26) Gene Expression In Enterocyte–like Colon Cancer Cell Lines HT–29 And Caco–2: Cloning Of The Complete Human Coding Sequence And Changes Of Dipeptidyl Peptidase IV mRNA levels During Cell Differentiation," *J. Of Biological Chemistry* 267:220–2208 (1992). Abstract only.

Tanaka, T., et al., "Cloning And Functional Expression Of The T Cell Activation Antigen CD26", *J. Of Immunol.* 149: 481–486 (1992); published erratum appears in *J. Immunol.* 50(5): 2090 (Mar. 1993). Abstract only.

Heins, J., et al., "Mechanism Of Proline–Specific Proteinases: (1) Substrate Specificity of Dipeptidyl Peptidase IV From Pig Kidney And Proline–Specific Endopeptidase From *Flavobacterium Meningosepticum*", *Biochimica Et Biophysica Acta* 954:161–169 (1988). Abstract only.

Schon, E., et al., "Dipeptidyl Peptidase IV in The Immune System. Effects of Specific Enzyme Inhibitors On Activity Of Dipeptidyl Peptidase IV and Proliferation Of Human Lymphocytes", *Biological Chemistry* Hoppe Seyler 372:305–311 (1991). Abstract only.

Schon, E., et al., "The Dipeptidyl Peptidase IV, A Membrane Enzyme Involved In The Proliferation . . . Lymphocytes", *Biomedica Biochimica Acta* 44 (1985). Abstract only.

Schon, E., et al., "Dipeptidyl Peptidase IV in Human Lymphocytes. An Approach To The Role Of A Membrane Peptidase In The Immune System", *Biomedica Biochimica Acta* 45:1523–1528 (1986) Abstract only.

Schon, E., et al., "The Role Of Dipeptidyl Peptidase IV in Human T Lymphocyte Activation. Inhibitors And Antibodies Against Dipeptidyl Peptidase IV Suppress Lymphocyte Proliferation And Immunoglobulin Synthesis In Vitro", *Eur. J. Of Immunol.* 17:1821–1826 (1987). Abstract only.

Freeman, et al., "*Clinical & Experimental Immunology*" 88 (2): 275–279 (May 1992). Abstract only.

Perry, et al., *Eur. J. Of Immunol.* 26 (1): 136–141 (Jan. 1996). Abstract only.

Goodstone, et al., *Annals Of The Rheumatic Diseases* 55 (1):40–46 (Jan. 1996). Abstract only.

Hall, et al., *Seminars In Dermatology,* 10 (3):240–245 (Sep. 1991). Abstract only.

Karges, et al., *Molecular Aspects Of Medicine* 16(2):29–213 (1995). Abstract only.

Short, et al., *Nephrol Dial Transplant* (Supp. 1) pp. 1–121 (1992). Abstract only.

Kalluri, et al., *J. Of The American Society Of Nephrology* 6 (4):1178–1185 (Oct. 1995). Abstract only.

Mullins, et al., *J. Of Clinical Investigation* 96 (1): 30–37 (Jul. 1996). Abstract only.

El Far, et al., *J. Of Neurochemistry,* 64 (4): 1696–1702 (Apr. 1995). Abstract only.

James, et al., *Clinical & Experimental Rheumatology,* 13 (3):299–305 (May–Jun. 1995). Abstract only.

Van Noort, et al., *Nature* 375 (6534):798–801 (Jun. 29, 1995). Abstract only.

Protti, et al., *Immunol. Today* 14 (7): 363–368 Jul. 1993). Abstract only.

Linington, et al., *Eur. J. Of Immunol.* 22 (7): 1813–1817 (Jul. 1992). Abstract only.

Chan, et al., *Archives Of Ophthalmology* 113 (5): 597–600 (May 1995). Abstract only.

Liu, et al., *J. Of Immunol.* 155 (11): 5449–5454 (Dec. 1995). Abstract only.

Uibo, et al., *J. Of Autoimmunity* 7 (3): 399–411 (Jun. 1994). Abstract only.

Kokawa, et al., *Eur. J. Of Hematology* 50 (2): 74–80 (1993). Abstract only.

Daw, et al., *J. Of Immunol.* 156 (2): 818–825 (Jan. 15, 1996). Abstract only.

Chazenblak, et al., *J. Of Clinical Investigation* 92 (1):62–74 (Jul. 1993). Abstract only.

Hart, et al., *Pharmaceutical Biotechnology* 6:821–845 (1995). Abstract only.

Lopez, et al., *Vaccine* 12 (7):585–591 (1994). Abstract only.

Reynolds, et al., *J. Of Immunol.* 152 (1):193–200 (Jan. 1, 1994). Abstract only.

Nardelli, et al., *J. Of Immunol.* 148 (3): 914–920 (Feb. 1, 1992). Abstract only.

Darcy, et al., *J. Of Immunol.* 149 (11):3636–3641 (Dec. 1, 1992). Abstract only.

Ritu, et al., *Vaccine* 10 (11): 761–765 (1992). Abstract only.

Ikagawa, et al., *J. Of Allergy & Clinical Immunol.* 97 (1 Pt 1): 53–64 (Jan. 1996). Abstract only.

Brander, et al., *J. Of Immunol.* 155 (5):2670–2678 (Sep. 1, 1995). Abstract only.

O'Brien, et al., *Immunology* 86 (2):176–182 (Oct. 1995). Abstract only.

Zhu et al., *J. Immunol* 155(10), pp. 5064–5073 (Nov. 1995). Abstract only.

Dudler, et al., *Eur. J. Of Immunol.* 25 (2):538–542 (Feb. 1995). Abstract only.

Bungy, et al., *Eur. J. Of Immunol.* 24 (9):2098–2103 (Sep. 1994). Abstract only.

Shimojo, et al., *Int'l. Archives Of Allergy & Immunol.* 105 (2): 155–161 (Oct. 1994). Abstract only.

Kelly, T.A., et al., "The Efficient Synthesis And Simple Resolution Of A Proline Boronate Ester Suitable For Enzyme Inhibition Studies", *Tetrahedron* 49:1009–1016 (1993). Abstract only.

Watson, J.D., "Continuous Proliferation Of Murine Antigen Specific Helper T Lymphocytes In Culture", *J. Of Experimental Medicine* 150:1510 (1979). Abstract only.

Kuchroo, V.K., et al., "Induction Of Experimental Allergic Encephalomyelitis By Myelin Proteolipid–Protein– Specific T Cell Clones And Synthetic Peptides", *Pathobiology* 59:305–312 (1991). Abstract only.

Kuchroo, V.K., et al., "T–cell Receptor Alpha Chain Plays a Critical Role In Antigen–Specific Suppressor Cell Function", *Proceedings Of The Nat'l. Academy Of Sciences Of The United States Of America* 88:8700–8704 (1991). Abstract only.

Kuchroo, V.K., et al., "Experimental Allergic Encephalomyelitis Medicated Cloned T Cells Specific For a Synthetic Peptide of Myelin Proteolipid Protein. Fine Specificity And T Cell Receptor V Usage", *J. Of Immunol.* 148:3776–3782 (1992). Abstract only.

Kuchroo, V.K., et al., "Cytokines And Adhesion Molecules Contribute To The Ability Of Myelin Proteolipid Protein-Specific T Cell Clones To Mediate Experimental Allergic Encephalomyelitis", *J. Of Immunol.* 151:4371–4382 (1993). Abstract only.

Kuchroo, V.K., et al., "T Cell Receptor (TCR) Usage Determines Disease Susceptibility In Experimental Autoimmune Encephalomyelitis: Studies with TCR V Beta *. 2 Transgenic Mice", *J. Of Experimental Medicine* 179:1659–1664 (1994). Abstract only.

Kuchroo, V.K. et al., "A Single TCR Antagonist Peptide Inhibits Experimental Allergic Encephalomyelitis Mediated By A Diverse T Cell Repertoire", *J. Of Immunol.* 153:3326–3336 (1994). Abstract only.

Jorgensen, J.L., et al., "Molecular Components Of T–Cell Recognition," *Ann. Rev. Immunol.* 10:835–873 (1992). Abstract only.

Wyse–Coray, T., et al., "Use Of Antibody/Peptides Constructs Of Direct Antigenic Peptides To T Cells: Evidence For T Cells Processing And Presentation", *Cellular Immunol.* 139 (1):268–73 (1992). Abstract only.

Panina–Bordignon, P., et al., "University Immunogenic T Cell Epitopes: Promiscuous Binding To Human MHC Class II And Promiscuous Recogniton By T Cells", *Eur. J. Immunol.* 19:2237–2242 (1989). Abstract only.

Ebenbichler, C., et al., "Structure–function Relationships Of The HIV–1 Envelope V3 Loop Tropism Determinant: Evidence For Two Distinct Conformations", *Aids* 7:639–46 (1993). Abstract only.

Linsley, P.S., et al., "Effects Of Anti–gp120 Monoclonal Antibodies On CD4 Receptor Binding By The Env Protein Of Human Immunodeficiency Virus Type 1", *J. Of Virology* 62:3695–3702 (1988). Abstract only.

Rini, J.M., et al., "Crystal Structure Of A Human Immunodeficiency Virus Type 1 Neutralizing Antibody, 50.1, In Complex With Its V3 Loop Peptide Antigen", *Proceedings Of The Nat'l. Academy of Sciences Of The United States Of America* 90:6325–9 (1993). Abstract only.

Subramanyam, W.G., et al., "Mechamism Of HIV–1 Tat Induced Inhibition Of Antigen–Specific T Cell Responsiveness", *J. Of Immunol.* 150:2544–2553 (1993), Abstract only.

Dang, N.H., et al., "Cell Surface Modulation Of CD26 By Anti–1F7 Monoclonal Antibody: Analysis Of Surface Expression And Human T Cell Activation", *J. Of Immunol.* 145:3963–3971 (1990). Abstract only.

De Caestecker, M.P ., et al., "The Detection Of Intercytoplasmic Interleukin 1 (Alpha) Expression In Human Monocytes Using Two Colour Immunoflourescence Flow Cytometry", *J. Immunol. Methods* 154:11–20 (1992). Abstract only.

Fauci, A.S., "The Human Immunodeficiency Virus: Infectivity And Mechanisms Of Pathogenesis", *Science* 239:617–722 (1988). Abstract only.

Kinder, D ., et al., "Analogues of Carbamyl Aspartate as Inhibitors . . . " *J. Med. Chem,* (1990), 33:819–823.

Snow, R., et al., "Studies on Proline Boronic Acid Dipeptide Inhibityors of Dipeptidyl . . . " *J. Med. Chem,* (1990), 116:10860–10869.

Wijdenes et al., "Monoclonal Antibodies (mAb) against gp130 Imitating Cytokines Which Use the gp130 for Signal Transduction", (Jul. 1995), p. 303.

Blumenstein et al., "Synthetic Non–Peptide Inhibitors of HIV Protease," vol. 163, No. 2 (1989), pp. 980–987.

Luftig et al., "Update on Viral Pathogenesis," ASM News (1990) vol. 56, No. 7, pp. 366–368.

Jiang et al., "Inhibition of Human Immunodeficiency Virus Type 1 Infection in a T–Cell Line (CEM) by New Dipeptidyl–Peptides IV (CD26) Inhibitors," *Res. Virol.* (1997), vol. 148, pp. 255–266.

Coutts et al., "Structure–Activity Relationships of Boronic Acid Inhibitors of Dipeptidyl Peptidase IV, 1. Variation of the $P_2$ Position of $X_{22}$–boroPro Dipeptides," *J. Med. Chem.* (1996), vol. 39, pp. 2087–2094.

Ostresh et al., "Generation of Use of Nonsupport–Bound Peptide and Peptidomimetic Combinatorial Libraries," *Methods in Enzymology,* (1996) vol. 267, pp. 230–234.

Bristol, L, et al., "Inhibition of CD26 Enzyme Activity with Pro–boropro Stimulates Rat Granulocyte/Macrophage Colony Formation and Thymocyte Proliferation in Vitro," *Blood,* vol. 85, No. 12 (1995), pp. 3602–3609.

Ansorge S., et al., "CD26/Dipeptidyl Peptidase IV in Lymphocyte Growth Regulation," *Advances in Medicine and Biology,* (1997), vol. 421, pp. 127–40.

Reinhold, Dirk, et al., "Inhibitors of Dipeptidyl PepdaseIV (DP IV, CD26) Induces Secretion of Transforming Growth Factor–$\beta$1 . . . ", *Immunology Letters,* 58(1997), pp. 29–35.

* cited by examiner

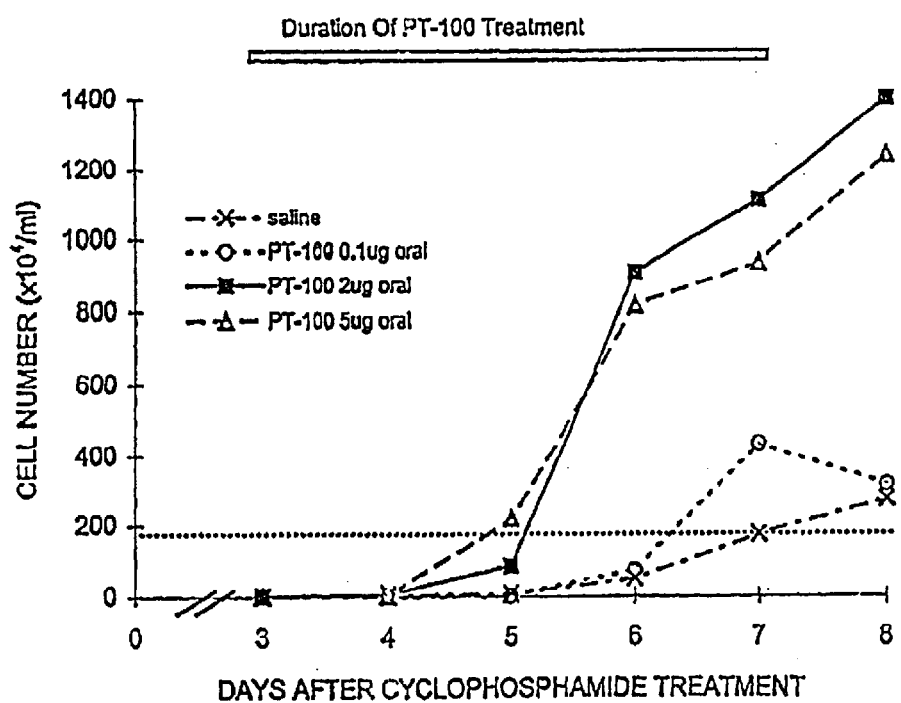

Stimulation of Hematopoiesis in the Spleen of Normal Mice

HEMATOPOIETIC STIMULATION

RELATED APPLICATIONS

This application is a continuation application of prior U.S. patent application Ser. No. 09/304,199, filed May 3, 1999, entitled Hematopoietic Stimulation, now issued as U.S. Pat. No. 6,300,314 B1 the entire contents of which are incorporated herein by reference and which claims priority under 35 U.S.C. § 119(e) to U.S. provisional application serial No. 60/084,128 filed May 4, 1998.

BACKGROUND OF THE INVENTION

The present invention relates to methods and products for producing increased numbers of hematopoietic cells, of restoring to preselected normal levels numbers of hematopoietic cells, to therapies for treating deficiencies in hematopoietic cells and to in vitro methodologies for culturing hematopoietic cells.

PT-100 is a dipeptide consisting of valine-prolineboronic acid (ValboroPro) designed to interact with the cell surface receptor CD26. CD26, a type II transmembrane protein is expressed on the cell surface of a number of cell types, including lymphocytes (Marguet, D. et al., *Advances in Neuroimmunol.* 3:209–215 (1993)), hematopoietic cells (Vivier, I. et al., *J. Immunol.* 147:447–454 (1991); Bristol, et al., *J. Immunol.* 149:367 (1992)) thymocytes (Dang, N. H. et al., *J. Immunol.* 147:2825–2832 (1991), Tanaka, T. et al., *J. Immunol.* 149:481–486 (1992), Darmoul, D. et al., *J Biol. Chem.* 267:4824–4833 (1992)), intestinal brush border membrane and endothelial cells. Cell surface associated CD26 is a sialoglycoprotein, with most of its mass on the outside of the cell.

CD26 has been best characterized on peripheral T cells where it functions as a potent costimulatory signal for T cell activation. Its surface expression is upregulated upon T cell activation (Dong, R. P. et al., *Cell* 9:153–162 (1996), Torimoto, Y. et al., *J. Immunol* 147:2514 (1991), Mittrucker, H-W. et al., *Eur. J Immun.* 25:295–297 (1995), Hafler, D. A. et al., *J. Immunol.* 142:2590–2596 (1989), Dang, N. H. et al., *J. Immunol* 144:409 (1990)). CD26 has also been identified in rodents as an important regulatory surface receptor in hematopoiesis and lymphoid development (Vivier, I. et al., *J. Immunol.* 147:447–454 (1991)). The primary structure of CD26 is highly conserved between species (Ogata, S. et al., *J. Biol. Chem.* 264:3596–3601 (1998)). In humans CD26 seems to be involved in the regulation of thymocyte activation, differentiation and maturation (Dang, N. H. et al., *J. Immunol.* 147:2825–2832 (1991); Kameoka, J. et al., *Blood* 85:1132–1137 (1995)). We have evidence that CD26 is expressed within the human and murine hematopoietic systems.

CD26 is an ectoenzyme with activity identical to that of Dipeptidyl Peptidase IV (DPP-IV), a serine type exopeptidase with high substrate specificity. It cleaves N-terminal dipeptides from proteins if the penultimate amino acid is proline, or in some cases alaninie (Fleischer, B. *Immunol. Today* 15:180 (1994)). PT-100 is a potent inhibitor of DPP-IV activity.

The prior art PCT published application WO94/03055 teaches methods of producing increased numbers of hematopoietic cells by administering inhibitors of DPP-IV. The teaching of this published application, however, is that dosages of at least 1 mg/kg body weight are necessary to achieve such hematopoietic cell increases. This published application also teaches that inhibitors are administered to mammals which have an established deficiency of hematopoietic cells. The teaching also suggests that cytokines be administered in conjunction with the inhibitors to increase the production of hematopoietic cells in a subject.

SUMMARY OF THE INVENTION

The invention is based upon a variety of surprising and unexpected findings. It has been discovered, unexpectedly, that the agents useful according to the invention stimulate growth factor production by stromal cells. It also has been discovered, unexpectedly, that the agents useful according to the invention stimulate proliferation of primitive hematopoietic progenitor cells, but do not stimulate directly the differentiation or proliferation of committed progenitor cells. It further has been discovered, unexpectedly, that the agents useful according to the invention can be administered at doses much lower than would have been expected according to the teachings of the prior art. Another unexpected finding is that the agents according to the invention can accelerate the time it takes to achieve hematopoietic cell recovery after treatment with an hematopoietic cell inhibitor. Another unexpected finding is that the agents useful according to the invention can at relatively low doses, restore normal levels of neutrophils at least as fast as the most successful commercially available product used worldwide for this purpose, except that the agents useful according to the invention can be used orally, whereas the commercially available product (which represents more than a billion dollar market) must be injected. These unexpected results have important therapeutic and experimental research implications.

According to one aspect of the invention, a method is provided for treating a subject to stimulate hematopoiesis in the subject. The invention involves administering to a subject in need of such treatment an amount of an agent effective to increase the number of hematopoietic cells or mature blood cells in the subject, wherein the amount is less than 1 mg/kg body weight per day and wherein the agent is a compound of Formula I.

The agents useful according to the invention are compounds of Formula I:

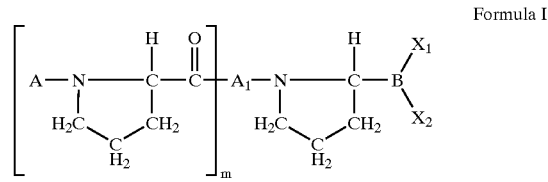

Formula I wherein m is an integer between 0 and 10, inclusive; A and $A_1$ are L-amino acid residues (for glycine there is no such distinction) such that the A in each repeating bracketed unit can be a different amino acid residue; the C bonded to B is in the L-configuration; the bonds between A and N, $A_1$ and C, and between $A_1$ and N are peptide bonds; and each X, and $X_2$ is, independently, a hydroxyl group or a group capable of being hydrolysed to a hydroxyl group in aqueous solution at physiological pH. By "the C bonded to B is in the L-configuration" is meant that the absolute configuration of the C is like that of an L-amino acid.

Thus, the

group has the same relationship to the C as the —COOH group of an L-amino acid has to its α carbon. In some embodiments, A and $A_1$ are independently proline or alanine residues; m is 0; $X_1$ and $X_2$ are hydroxyl groups; the inhibitor is L-Ala-L-boroPro; and the inhibitor is L-Pro-L-boroPro.

In one important aspect of the invention, the subject has an abnormally low level of hematopoietic cells or mature blood cells and the agent is administered in an amount effective to restore levels of a hematopoietic cell-type or mature blood cell-type to a preselected normal or protective level. The agent preferably is administered to the subject in at least 2 doses in an 18 hours period. The invention has particularly important applications in the restoration of normal or protective levels of neutrophils, erythrocytes and platelets. The most preferred agent is ValBoroPro.

According to another aspect of the invention, a method is provided for shortening or eliminating the time that a subject has an abnormally low level of hematopoietic or mature blood cells resulting from treatment with a hematopoietic cell inhibitor. An agent is administered to a subject in need of such treatment in an amount effective to increase the number of hematopoietic cells or mature blood cells in the subject, wherein the administration of the agent begins prior to or substantially simultaneous with administration of the hematopoietic cell inhibitor. The agents and the preferred agent are as described above. In one important embodiment, the hematopoietic cell inhibitor causes an abnormally low level of hematopoietic cells or mature blood cells in the subject and the agent is administered in an amount effective to restore levels of a hematopoietic cell type to a preselected normal or protective level. Preferably, the agent is administered to the subject in at least 2 doses in an 18 hour period. In important embodiments, the agent is used to restore in the subject normal or protective levels of neutrophils, erythrocytes or platelets. The preferred effective amount of agent is as described above.

According to another aspect of the invention, a method is provided for preparing a subject for treatment with a hematopoietic cell inhibitor. The method involves administering to the subject prior to the subject receiving the hematopoietic cell inhibitor an agent in an amount effective to stimulate in the subject production of growth factors. In one embodiment the agent stimulates stromal cell production of growth factor. The agents and the preferred agent are as described above. In one important embodiment, the growth factor is granulocyte colony stimulating factor. In other embodiments the growth factor is selected from the group consisting of IL-1, IL-2, IL-3, IL-4, IL-6, IL-11, IL-17, TPO, EPO, MCSF, GMCSF, FLT-3 Ligand and Stem Cell Factor. Preferably, the amount administered to the subject is less than 1 mg/kg body weight per day. It also is preferred that the administration of the agent be in at least 2 doses of the agent in an 18 hour period.

According to another aspect of the invention, a method is provided for treating a subject to increase the number of hematopoietic cells or mature blood cells in the subject. An agent is administered to a subject in need of such treatment in an amount effective to increase hematopoietic cells or mature blood cells in the subject, wherein the agent is administered in a first regimen consisting of 2 doses or 3 doses in an 18 hour period. The agents and the preferred agent are as described above. In one important embodiment, the agent is administered in a second regimen consisting of 2 doses or 3 doses in an 18 hours period, wherein the second regimen is separate in time from the first regimen. In another embodiment, the agent is administered in a third regimen consisting of 2 doses or 3 doses in an 18 hour period, wherein the third regimen is separate in time from the first and second regimens. In other embodiments, the agent is administered optionally in a fourth regimen, a fifth regimen, a sixth regimen, or a seventh regimen, wherein each of such regimens consists of 2 doses or 3 doses in an 18 hours period, and wherein the regimens are separate in time from one another and from the prior regimens. In one important embodiment, the subject has an abnormally low neutrophil count and the amount is effective to restore in the subject a preselected level of neutrophils. In other important embodiments the subject has abnormally low levels of erythrocytes and platelets. The preferred dosages, agents, and the like are as described above. In important embodiments, the dosage is no more than six regimens, no more than five regimens, no more than four regimens, no more than three regimens, and even no more than two regimens.

According to another aspect of the invention, a method is provided for preparing a subject's cells for reintroduction into the subject. The method involves treating the subject with an agent in an amount effective to stimulate in the subject the hematopoietic cells, then collecting the hematopoietic cells from the subject. The collected cells later are reintroduced into the subject. The collected cells optionally can be ex vivo cultured. The agents and preferred agent are as described above. In one embodiment, the ex vivo culturing is carried out in the presence of an amount of the agent effective to stimulate proliferation of the collected cells. In another embodiment, the concentration of the agent in medium surrounding the collected cells is less than $10^{-8}$ moles per liter, and less than $10^{-9}$ moles per liter and even less than $10^{-10}$ moles per liter.

According to another aspect of the invention, a method is provided for stimulating growth factor production by stromal cells. The method involves contacting the stromal cells with an agent in an amount effective to stimulate growth factor production by the stromal cells. The agents and the preferred agent are as described above. In one embodiment, the stromal cells are in an in vitro layer of stromal cells for supporting early progenitor cell growth and further comprising culturing the stem cells in the presence of these stromal cells. In another embodiment, the stromal cells are in vivo in a subject. In another embodiment, the growth factor is granulocyte colony stimulating factor. In other embodiments the growth factor is selected from the group consisting of IL-1, IL-2, IL-3, IL-4, IL-6, IL-11, IL-17, TPO, EPO, MCSF, GMCSF, FLT-3 Ligand and Stem Cell Factor. In an in vivo embodiment, the agent is administered to a subject in an amount less than 1 mg/kg body weight per day. In still another embodiment, the stem cells are cultured in an environment free of exogenously added granulocyte colony stimulating factor. In important embodiments the stromal cells are bone marrow or thymic stromal cells.

According to another aspect of the invention, a kit is provided for treating a subject having an abnormally low level of hematopoietic cells resulting from treatment with a hematopoietic cell inhibitor or for treating prophylactically a subject being treated with a hematopoietic cell inhibitor to prevent decrease or loss of hematopoietic and/or mature blood cells. The kit is a package containing a first dosage and instructions for treating a subject substantially simultaneous with or prior to treatment with the hematopoietic cell inhibitor. The package also contains a second dosage and instructions for treating a subject only after treatment with the hematopoietic cell inhibitor. The dosages are in effective amounts and the agents and preferred agent are as described above. In one embodiment, the second dosage is between 2 and 5 regimens, each of the regimens consisting of 2 or 3 doses per day of the agent. In one embodiment, the combination of the doses is less than 1 mg/kg body weight per day. One preferred kit is for treatment of neutropenia. Other preferred kits are for treatment of an abnormally low level of erythrocytes or platelets.

According to still another aspect of the invention, a kit is provided for treating a subject having abnormally low level of hematopoietic cells. The kit is a package containing a complete dosage for restoring normal levels of a hematopoietic cell type. The package consists essentially of: (1) a first dosage in an effective amount for administration to the subject during a first day, (2) a second dosage in an effective amount for administration to the subject during a second day, (3) optionally, a third dosage in an effective amount for administration to the subject during a third day, (4) optionally, a fourth dosage in an effective a mount for administration to the subject during a fourth day, (5) optionally, a fifth dosage in an effective amount for administration to the subject during a fifth day, (6) optionally, a sixth dosage in an effective amount for administration to the subject during a sixth day and (7) optionally, a seventh dosage in an effective amount for administration to the subject during a seventh day. The agents and preferred agent are as described above. In one important embodiment, each of the dosages consists of 2 or 3 doses of the agent for administration each day. Preferred doses and dosages are as described above. In important embodiments, the kit consists essentially of less than 5, less than 4, and less than 3 and even less than 2 dosages.

These and other aspects of the invention will be described in greater detail below.

BRIEF DESCRIPTION OF THE DRAWINGS

FIG. 1 is a medicinal package for administering a 5 day medicinal course of treatment for treating myelosuppression or anemia resulting from cancer chemotherapy.

FIG. 2 is a graph depicting the regeneration of neutrophils in cyclophosphamide-treated mice. PT-100 at indicated doses or saline administered by gavage. Absolute neutrophil counts in mice not treated with cyclophosphamide are on the average $190 \times 10^4$ cells/ml as indicated by the dashed horizontal line.

DETAILED DESCRIPTION OF THE INVENTION

Figure 3:
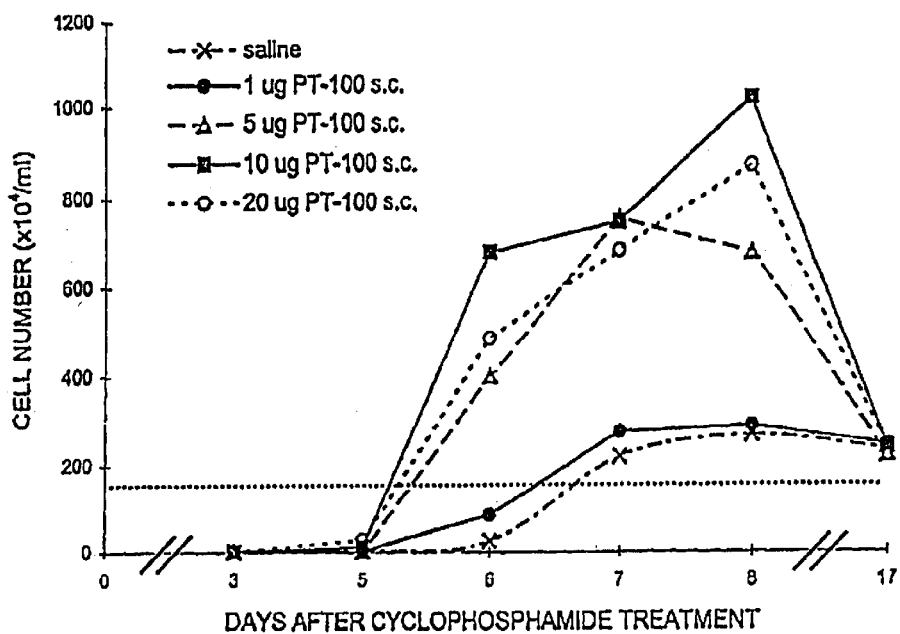
FIG. 3 is a graph depicting the regeneration of neutrophils in cyclophosphamide-treated mice in response to subcutaneous administration of PT-100. Saline or PT-100 were administered b.i.d. for 5 consecutive days. The average absolute neutrophil count in mice not treated with cyclophosphamide was $185 \times 10^4$ cells/ml as indicated by the horizontal dashed line.

The invention involves the stimulation of proliferation, differentiation and mobilization of hematopoietic cells. The invention is useful whenever it is desirable to stimulate the proliferation or differentiation, of or to mobilize, hematopoietic cells. Mobilization of hematopoietic cells is characterized by the enrichment of early progenitor cells in the bone marrow and the recruitment of these cells to the periphery in response to a mobilization agent (e.g. G-CSF, GM-CSF, etc.). The agents useful according to the invention can be used to inhibit hematopoietic cell deficiencies or to restore hematopoietic and mature blood cell count in subjects with such deficiencies. Such agents also may be used in connection with hematopoietic cell transplants, such as bone marrow or peripheral blood transplants, when used to replenish or create an immune system in a subject. The agents further can be used as an immune booster. The agents also are useful in vitro in connection with the culturing of cells for therapeutic and research uses.

As used herein, subject means humans, nonhuman primates, dogs, cats, sheep, goats, horses, cows, pigs and rodents.

One important aspect of the invention involves restoring or preventing a deficiency in hematopoietic cell number in a subject. Such deficiencies can arise, for example, from genetic abnormalities, from disease, from stress, from chemotherapy (e.g. cytotoxic drug treatment, steroid drug treatment, immunosuppressive drug treatment, etc.) and from radiation treatment.

The invention is useful in general to restore deficiencies created by hematopoietic cell inhibitors. A hematopoietic cell inhibitor is an exogenously-applied agent (such as a drug or radiation treatment) which causes a decrease in the subject of hematopoietic cells and/or mature blood cells.

Hematopoietic cells as used herein refer to granulocytes (e.g. promyelocytes, neutrophils, eosinophils and basophils), erythrocytes, reticulocytes, thrombocytes (e.g. megakaryoblasts, platelet-producing megakaryocytes and platelets), lymphocytes, monocytes, dendritic cells and macrophages. Mature blood cells consist of mature lymphocytes, platelets, erythrocytes, reticulocytes, granulocytes and macrophages. In certain important aspects of the invention, the agents useful according to the invention increase the number of neutrophils, erythrocytes and platelets. In connection with neutrophils, the agents may be used to treat, inter alia, drug or radiation-induced neutropenia, chronic idiopathic neutropenia and cyclic neutropenia.

One important aspect of the invention is restoring in a subject "normal" or "protective" hematopoietic cell levels. A "normal" level as used herein can be a level in a control population, which preferably includes subjects having similar characteristics as the treated individual, such as age. The "normal" level can also be a range, for example, where a population is used to obtain a baseline range for a particular group into which the subject falls. The population can also be divided into groups, such as into quadrants, with the lowest quadrant being individuals with the lowest levels of hematopoietic cells and the highest quadrant being individuals having the highest levels of hematopoietic cells. Thus, the "normal" value can depend upon a particular population selected. Preferably, the normal levels are those of apparently healthy subjects which have no prior history of hematopoietic cell disorders. Such "normal" levels, then can be established as preselected values, taking into account the category in which an individual falls. Appropriate ranges and categories can be selected with no more than routine experimentation by those of ordinary skill in the art. Either the mean or another preselected number within the range can be established as the normal preselected value. Likewise, the level in a subject prior to treatment with a hematopoietic cell inhibitor can be used as the predetermined value.

In general, the normal range for neutrophils is about 1800–7250 per $\mu$l (mean –3650); for basophils 0–150 per $\mu$l (mean –30); for eosinophils 0–700 per $\mu$l (mean –150); for macrophages and monocytes 200–950 per $\mu$l (mean –430); for lymphocytes 1500–4000 per $\mu$l (mean –2500); for erythrocytes $4.2 \times 10^6$–$6.1 \times 10^6$ per $\mu$l; and for platelets $133 \times 10^3$–$333 \times 10^3$ per $\mu$l. The foregoing ranges are at the 95% confidence level.

In connection with certain conditions, the medical community has established certain preselected values. For example, mild neutropenia is characterized as having a count of between 1000 and 2000 per $\mu$l, moderate neutropenia at between 500 and 1000 per $\mu$l and severe neutropenia at below 500 per $\mu$l. Likewise, in adults, a lymphocyte count at less than 1500 is considered a medically undesirable condition. In children the value is less than 3000. Other preselected values will be readily known to those of ordinary skill in the art. The agents useful according to the invention can be used to establish or to re-establish such preselected values, including normal levels.

Protective levels of hematopoietic cells is the number of cells required to confer clinical benefit to the patient. The required levels can be equal to or less than "normal levels". Such levels are well known to those of ordinary skill in the art. For example, a protective level of neutrophils is above 1000, preferably, at least 1500.

According to another aspect of the invention, the agents useful herein can be applied at doses below those which were described in the prior art. In particular, it has been discovered unexpectedly that the agents of the invention can be administered in doses less than 1 mg/kg body weight per day. In particular, the agents of the invention have been used successfully at levels of 0.1 mg/kg body weight per day, which is one order of magnitude below the teachings of the prior art. As will be readily recognized by those of ordinary skill in the art, this has advantages in that less material is required for treatment, thereby lessening any risk of side effects. Likewise, this has advantages in connection with the cost of manufacture of the drug products of the invention.

According to another aspect of the invention, better therapeutic results can be achieved when the agents are applied in multiple doses per day. This finding is unexpected and, additionally, it has been found that there is no added medically useful effect when the agents useful according to the invention are administered for lengthy periods of time. Thus, it has been discovered, unexpectedly, that only very brief periods of treatment are needed to achieve established therapeutic goals.

As described in the examples below, subjects treated with the agents useful according to the invention in 2 doses per day versus 1 dose per day achieved recovery of hematopoietic cells almost 33% faster than subjects receiving only 1 dose per day. Surprisingly, this result did not depend upon the absolute amount of drug given to the subject, but instead related to the number of times the subject was administered the drug. In other words, as shown below, giving twice as much drug, but only once a day, did not speed the recovery of hematopoietic cell number. Thus, an aspect of the invention involves giving the agents useful according to the invention in 2 or 3 doses in an 18 hour period. As used herein, an 18 hour period refers in general to the time during which a subject is awake in any 24 hour period; it is intended to indicate 2 doses per day, 3 doses per day, and the like.

According to still another aspect of the invention, it has been discovered unexpectedly that the agents useful according to the invention need be administered for fewer days than expected according to the prior art. In particular, in the mouse models employed, there was very little difference in the speed of recovery of hematopoietic cell count and in the ability to reestablish normal levels of hematopoietic cells when treatment was 3 days, versus 4 days, versus 5 days. It is believed, therefore, that when applied to humans, a complete drug treatment will involve 7 days or less, more preferably 6 days or less, more preferably 5 days or less, more preferably 4 days or less, and even more preferably 3 days or less. As a result, the invention therefore provides kits which contain complete treatment packages for restoring hematopoietic cell count, which kits are described in greater detail below.

According to another aspect of the invention, the time that a subject has an abnormally low level of hematopoietic cells resulting from treatment with a hematopoietic cell inhibitor is shortened. It has been discovered, unexpectedly, that the agents used according to the invention stimulate growth factor production by stromal cells. For example, granulocyte colony stimulating factor (GCSF) production by stromal cells is stimulated. GCSF acts to drive specifically neutrophil-lineage differentiation. It does not affect the differentiation or proliferation of other committed hematopoietic cells, including other granulocytes, such as eosoniphils, basophils, mast cells and macrophages. (It is known to act synergistically, however, in vitro with other cytokines to affect proliferation of pluripotent stem cells, though the in vivo importance of this observation is not known). Because stromal cells are not rapidly dividing cells and are not generally adversely impacted by hematopoietic cell inhibitors, the agents useful according to the invention can be applied to subjects substantially simultaneously with or even prior to treatment with a hematopoietic cell inhibitor in order to stimulate stromal cells to produce growth factor which will be readily abundant and helpful in regenerating the hematopoietic cells after treatment by the hematopoietic cell inhibitor. In the prior art, such treatment has been delayed until substantially after treatment with the hematopoietic cell inhibitor. Substantially simultaneously with, as used herein, means within 24 hours of treatment with the hematopoietic cell inhibitor. Preferably, the agents useful according to the invention are administered within 2 hours of treatment with the hematopoietic cell inhibitor, if they are administered after treatment with the hematopoietic cell inhibitor. If they are administered before treatment with the hematopoietic cell inhibitor, then they are administered close enough in time to the treatment with the inhibitor so that stromal cell production of growth factor is enhanced in the days immediately following treatment with the hematopoietic cell inhibitor.

Another aspect of the invention involves treatment of a subject to prepare a subject for subsequent treatment with other agents. It has been discovered, unexpectedly, that the agents useful according to the invention stimulate the proliferation of primitive, noncommitted hematopoietic progenitor cells, but not directly the differentiation of committed progenitor cells. It is known in the art that such cells may or may not include $CD34^+$ cells. $CD34^+$ cells are immature cells present in blood products, express the CD34 cell surface marker, and are believed to include a subpopulation of cells with the capacity to self-renew and to differentiate into all of the mature blood cell types. Because the agents useful according to the invention stimulate the proliferation of such self-renewing cells, the invention is useful to prepare a subject for treatment with other exogenous growth factors and cytokines which in turn result in the differentiation of such uncommitted progenitor cells into committed progenitor cells. Likewise, the agents useful according to the invention can be administered to a subject to expand in the subject hematopoietic cells and to mobilize such cells, prior to extracting the cells from the subject for transplantation or re-infusion. Such cells may be used for research purposes or can be treated ex vivo or reintroduced into the subject with or without expansion in vitro.

The agents useful according to the invention can be administered in conjunction with exogenous growth factors and cytokines which are specifically selected to achieve a particular outcome. For example, if it is desired to stimulate a particular hematopoietic cell type, then growth factors and cytokines which stimulate proliferation and differentiation of such cell type are used. Thus, it is known that interleukins-1, 2, 3, 4, 5, 6, 7, 9, 10, 11, 12, 13 and 17 are involved in lymphocyte differentiation. Interleukins 3 and 4 are involved in mast cell differentiation. Granulocyte macrophage colony stimulating factor (GMCSF), interleukin-3 and interleukin-5 are involved in the eosinophil differentiation. GMCSF, macrophage colony stimulating factor (MCSF) and IL-3 are involved in macrophage differentiation. GMCSF, GCSF and IL-3 are involved in neutrophil differentiation. GMSCF, IL-3, IL-6, IL-11 and TPO are involved in platelet differentiation. Flt3 Ligand is involved in dendritic cell growth. GMCSF, IL-3, and erythropoietin are involved in erythrocycte differentiation. Finally, the self-renewal of primitive, pluripotent progenitor cells capable of sustaining hematopoiesis requires SCF, Flt3 Ligand, G-CSF, IL-3, IL-6 and IL-11. Various combinations for achieving a desired result will be apparent to those of ordinary skill in the art. Because the agents useful according to the invention stimulate primitive, non-committed hematopoietic progenitor cells, they can be used in connection with any of the foregoing categories of agents to stimulate specifically the proliferation of a particular hematopoietic cell type. The foregoing factors are well known to those of ordinary skill in the art, and most are commercially available.

The invention also lends itself to a variety of in vitro uses. Hematopoietic progenitor cells are preserved or expanded, or their colony forming unit potential increased, in vitro. One benefit that can be obtained according to the invention is the stimulation of hematopoietic progenitor cells by the agents useful according to the invention. Another benefit that can be obtained is the effect that the agent can have on stromal cells used in in vitro culturing of hematopoietic progenitor cells. In vitro culturing of hematopoietic cells is often carried out in the presence of stromal cells. Hematopoietic progenitor cells typically will not survive, proliferate or differentiate for very long periods of time in vitro without appropriate growth factor support.

Stromal cell layers are used to supply such growth agents to cultured hematopoietic cells, either by culturing the hematopoietic progenitor cells in vitro with such stromal cells or by supplying the hematopoietic progenitor cells with stromal cell-conditioned medium. The agents useful according to the present invention can be used to treat such stromal cells to cause the stromal cells to manufacture and release growth factors. The incubation of stromal cells with the agents useful according to the invention and in medium is for a period of time sufficient to allow the stromal cells to secrete factors into the medium. The medium then can be used to supplement the culture of hematopoietic progenitor cells and other hematopoietic cells.

The culture of hematopoietic cells is with media which is conventional for culturing cells. Examples include RPMI, DM, ISCOVES, etc. The conditions for such culturing also are known to those of ordinary skill in the art. The conditions typically refer to a combination of parameters (e.g. temperature, $CO_2$ and $O_2$ content, nutritive media, etc.). The time sufficient to increase the number of cells is a time that can be easily determined by a person skilled in the art, and can vary depending on the original number of cells seeded and the amount added of growth factors and agents useful according to the invention.

The colony forming potential of hematopoietic uncommitted progenitor cells can be increased by in vitro culturing of hematopoietic cells. The cells can be obtained from any blood product or organ containing cells of hematopoietic origin. Crude or unfractionated blood products can be enriched for cells having hematopoietic progenitor cell characteristics in ways well known to those of ordinary skill in the art, prior to or after culture with the agents useful according to the invention.

A particularly important aspect of the invention is in the use of the agents for treatment of neutropenia. A combination of unexpected results makes the invention particularly useful in the treatment of neutropenia. Firstly, the agents according to the invention can stimulate the proliferation of uncommitted progenitor cells. Secondly, the agents according to the invention also stimulate stromal cells to make GCSF, which is the growth factor critical in the differentiation and production of neutrophils per se. Thus, the patient has the dual benefit of stimulation of progenitor cells and differentiation of those cells into neutrophils using the agents useful according to the invention. Similar effects are shown with erythrocytes and platelets. Thus, treatment to restore neutrophils, erythrocytes and platelets form an independent and distinct aspect of the invention, based on the unexpected findings described above.

The invention also involves kits for housing an entire medicinal course of treatment for a hematopoietic cell deficiency such as neutropenia. As discussed above, it has been discovered surprisingly that the number of doses per day and the number of doses overall affect favorably the recovery of hematopoietic cells after treatment with a hematopoietic cell inhibitor. These unexpected findings lend themselves to the development of a medicinal dispenser which houses an entire medical course of treatment using the agents useful according to the invention. Patient compliance therefore will be enhanced, and an entire prescription can be contained in a single package. Ordinarily, a pharmacist individually fills a dispenser unit with a medicament once the pharmacist receives a doctor's prescription. Because the dispenser of the invention includes an entire medicinal course of treatment and can always include a specific number of solid oral dosage forms, the package can be pre-filled with the appropriate number of units of medicament for treatment for a particular medical purpose.

The medicinal dispenser is a package defining a plurality of medicinal storage compartments, each compartment for housing an individual unit of medicament. An entire medicinal course of treatment is housed in a plurality of medicinal storage compartments.

A package defining a plurality of medicinal storage compartments may be any type of disposable pharmaceutical package or card which holds medicaments in individual compartments. Preferably the package is a blister package constructed from a card, which may be made from stiff paper material, a blister sheet and backing sheet. Such cards are well known to those of ordinary skill in the art.

FIG. 1 shows a medicinal dispenser (1) for housing a preferred entire medicinal course of treatment for neutropenia. The day indicia (2) indicate which day the individual units of medicament are to be taken. These are marked along a first side of the medicinal package. The dose indicia (3) is marked along a second side of the medicinal package perpendicular to the first side of the medicinal package and indicates the time which the individual unit of medicament should be taken. The unit doses (4) are contained in the dispenser which is a blister pack. This particular package shows a 5 day course of treatment, with 2 doses per day.

The pharmaceutical preparations, as described above, are administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result. In some cases this is any increase in hematopoietic cell count or mature blood cell count. In other cases, it will be an increase to a preselected level.

The invention is useful in one aspect to ameliorate the effects of treatment with a hematopoietic cell inhibitor. If the agents are used prophylactically, they can decrease the amount of hematopoietic cells that would be lost in the subject versus the amount lost if the subject were treated with the inhibitor but not with the agent. If used prophylactically or acutely, the agents can shorten the time for recovery of a hematopoietic cell-type to at least protective levels, and preferably to normal levels, versus the length of time which would pass before protective or normal levels were achieved if the subject were treated with the inhibitor but not with the agent.

Generally, doses of active compounds of the present invention would be from about 0.01 mg/kg per day to less than 1 mg/kg per day. A variety of administration routes are available. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration is preferred for the convenience to the patient as well as the dosing schedule. See *Remington's Pharmaceutical Sciences*, 18th edition, 1990, pp 1694–1712; incorporated by reference). Those of skill in the art can readily determine the various parameters and conditions for producing dosages without resort to undue experimentation.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated.

The agents may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically acceptable salts can be prepared as alkaline metal or alkaline earth salts, such as sodium, potassium or calcium salts.

Other delivery systems can include time-release, delayed release or sustained release delivery systems. Such systems can avoid repeated administrations of the agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,667,014, 4,748,034 and 5,239,660 and (b) difusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

EXAMPLES

We have demonstrated in a series of in vivo studies that the agent ValboroPro (PT-100), has the ability to shorten myelosuppression caused by chemotherapy in mice. In these studies, mice were injected intraperitoneally with a sublethal dose of 220 mg/kg cyclophosphamide (Day 1). This treatment reproducibly induced a nadir in blood cell counts by Day 4. After 72 hours (Day 3) mice were divided into 3 groups. One group received PT-100, at the concentrations indicated, by gavage or by subcutaneous administration (s.c.), one group received G-CSF by s.c. injections and the third group received saline as a control, either by oral gavage or by s.c. injections. G-CSF was used at 0.04 ug/dose (4 $\mu$g/kg/day) which is the dose frequently used in published reports studying the G-CSF effects in mice and is also the equivalent dose used in cancer patients. All administrations were performed twice daily (b.i.d.) for 5 consecutive days or as indicated. Blood samples were taken from individual mice on Day 4–8, and in some experiments on Days 13 or 17. At each time pont four or five test animals were sampled. Total and differential white blood cell counts of Gimsa-stained blood smears were performed.

PT-100 Dose Response for Regeneration of Neutrophil

For data presented in FIG. 2, cyclophosphamide treated mice received 0.1 $\mu$g, 2 $\mu$g or 5 $\mu$g/b.i.d. of PT-100 or saline by oral gavage twice daily for 5 consecutive days starting on Day 3 post cyclophosphamide treatment and continuing through Day 7. In mice that received 2 or 5 $\mu$g/b.i.d. PT-100 recovery of neutrophils reproducibly preceded recovery of saline treated mice by 1 or 2 days, while 0.1 $\mu$g/b.i.d. of PT-100 did not significantly enhance neutrophil recovery over saline. Normal levels of absolute neutrophil counts (ANC) were reached on Day 5 for mice receiving 2 $\mu$g or 5 $\mu$g/b.i.d. of PT-100, while saline treated mice did not reach normal levels until Day 7. On Day 5 mice had received a total of 4 doses of PT-100 (on Days 3 and 4). Additional administration of PT-100 on Days 5, 6 and 7 caused a further increase in ANC.

The effect of PT-100 on neutrophil recovery when administered by s.c. route was very similar to that seen when administered orally. For data shown in FIG. 3 mice were injected s.c. with doses of PT-100 ranging from 1 to 20 $\mu$g/b.i.d. for 5 days and blood cell counts determined on Days 4 through 8, and on Day 17. For mice receiving 5 $\mu$g, 10 $\mu$g, or 20 $\mu$g/b.i.d. PT-100, neutrophil recovery was accelerated over that observed in the saline treated mice. A dose of 1 $\mu$g/b.i.d. PT-100 did not show much effect. After termination of treatment with PT-100, In conclusion, PT-100 accelerates neutrophil regeneration in cyclophosphamide treated mice.

Comparison of PT-100 and G-SCF Effects on Neutrophil Regeneration

Figure 4:
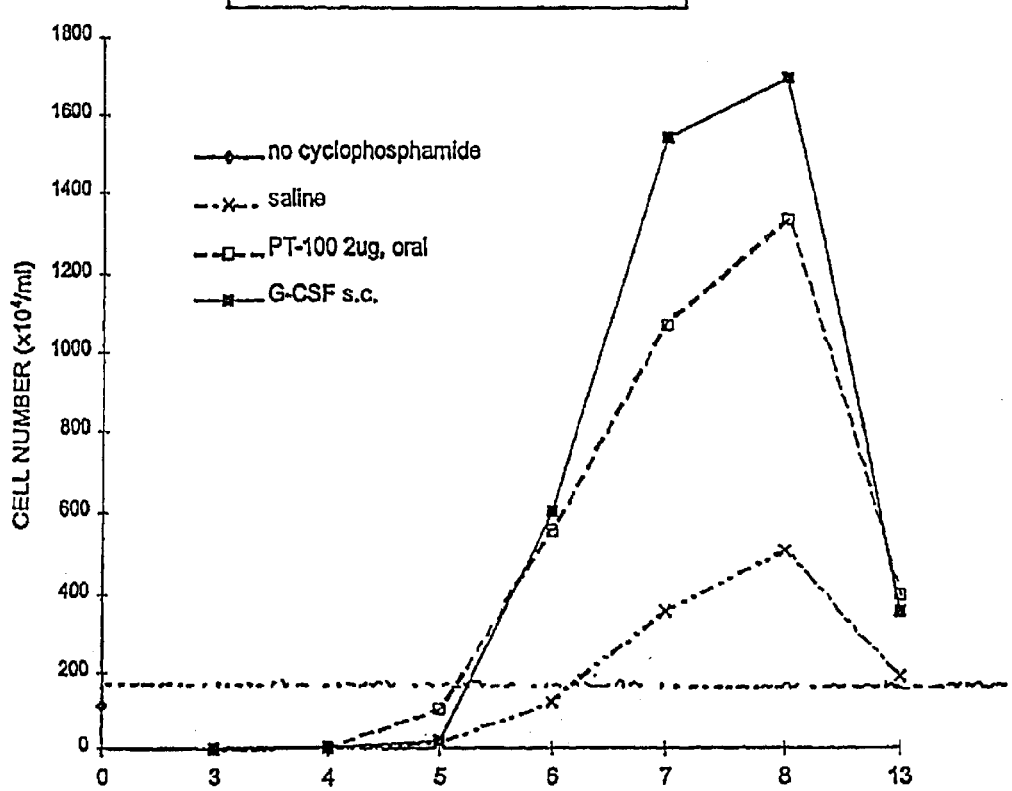
FIG. 4 is a graph depicting the regeneration of neutrophils in cyclophosphamide-treated mice in response to PT-100 and granulocyte colony stimulating factor. PT-100 in saline was administered by gavage, and GCSF by subcutaneous injections, for 5 days. Absolute neutrophil count in mice not treated with cyclophosphamide are on average $190 \times 10^4$ cells/ml as indicated by the dashed horizontal line.

G-CSF is currently used to accelerate neutrophil recovery in cancer patients undergoing chemotherapy. The effects of G-CSF in mice are well established and can be used as a reference for elucidating the mechanism by which PT-100 stimulates hematopoiesis in mice. FIG. 4 shows data from an experiment in which the effects of PT-100 and G-CSF on neutrophil regeneration are compared. Cyclophosphamide treated mice were administered 2 $\mu$g/b.i.d. of PT-100 by gavage or 0.04 $\mu$g/b.i.d. of G-CSF (the dose equivalent used in patients and most commonly used in published reports for murine studies) by subcutaneous injections for 5 consecutive days starting on Day 3. Blood cell counts were performed on Days 4–8, and on Day 13.

PT-100 and G-CSF treated mice stimulated neutrophil regeneration to a similar level during the treatment period. After treatment was stopped, ANC decreased to normal counts by Day 13. Although PT-100 has a very similar effect on neutrophil reconstitution, the mechanism of action is different from that of G-CSF. Not only does PT-100 target a different cellular receptor (CD 26), it also has been shown to stimulate growth of early human hematopoietic progenitor cells which are not affected by G-CSF.

Dose Numbering of PT-100 Administration

Figure 5:
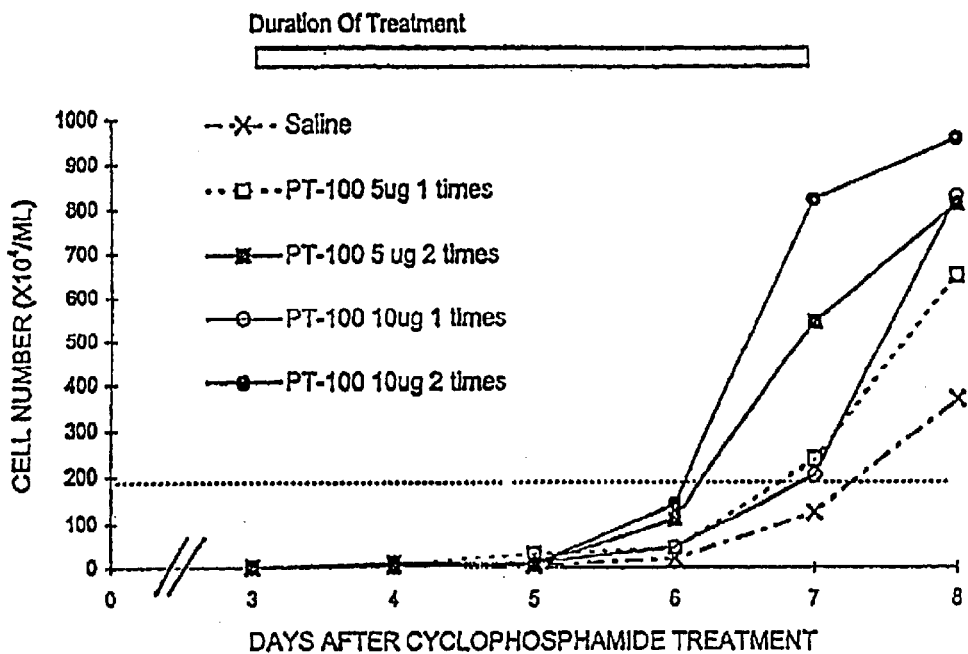
FIG. 5 is a graph depicting the effect of PT-100 dose number on the regeneration of neutrophils in cyclophosphamide-treated mice. PT-100, at indicated concentrations, was administered either once or twice per day subcutaneously for 5 days. The average absolute neutrophil count for mice not treated with cyclophosphamide was $200 \times 10^4$ cells/ml as indicated by the dashed horizontal line.

To determine the dose numbering of administration for optimal recovery of neutrophils, PT-100, at indicated doses, was administered s.c. to cyclophosphamide treated mice, either once or twice per day over a five day period, starting on Day 3 post cyclophosphamide treatment. As shown in FIG. 5, for both doses, a twice daily administration resulted in a faster rate of neutrophil recovery to higher neutrophil levels than once per day administration.

Duration of PT-100 Administration

In the experiments described above mice had been treated with PT-100 for 5 consecutive days. To determine whether a shorter period of treatment with PT-100 was sufficient for the recovery of neutrophils 5 µg, 2 µg, or 1 µg/b.i.d. (six hours apart) of PT-100 was administered to cyclophosphamide treated mice by gavage for 1, 2, 3, or 5 days starting on Day 3 post cyclophosphamide treatment. Blood counts were obtained on days 4 through 8.

Administration of PT-100 for one day was sufficient to cause an accelerated reconstitution of neutrophils over saline treated animals. However, additional administrations of PT-100 for 2 or 3 days increased the rate of recovery even further. Data for the 5 µg dose are shown in FIG. 6.

Figure 7:
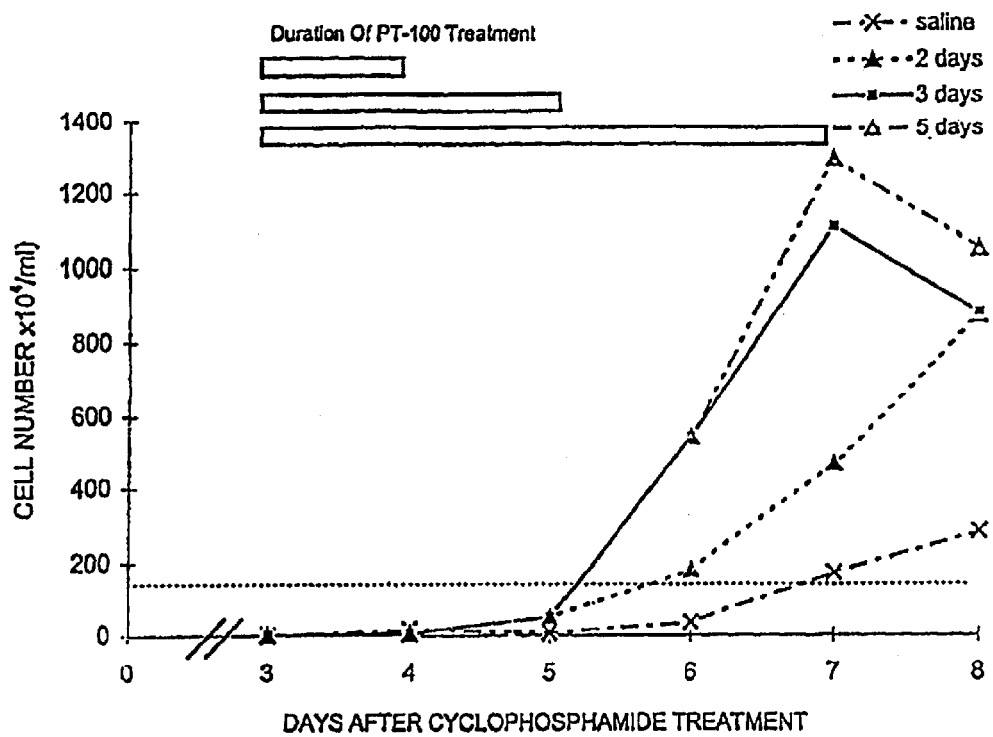
FIG. 7 is a graph showing the effect of duration of PT-100 treatment on the regeneration of neutrophils in cyclophosphamide-treated mice. PT-100 (2 µg/b.i.d.), or saline were administered by gavage for the indicated duration. The average absolute neutrophil count for mice not treated with cyclophosphamide was $194 \times 10^4$ cells/ml as shown by the dotted line.

Continued administration of PT-100 for a total of 4 or 5 days does not significantly increase the rate of neutrophil recovery or the ANC over that achieved with 3 day administrations (data for 2 µg/b.i.d. are shown in FIG. 7).

Figure 6:
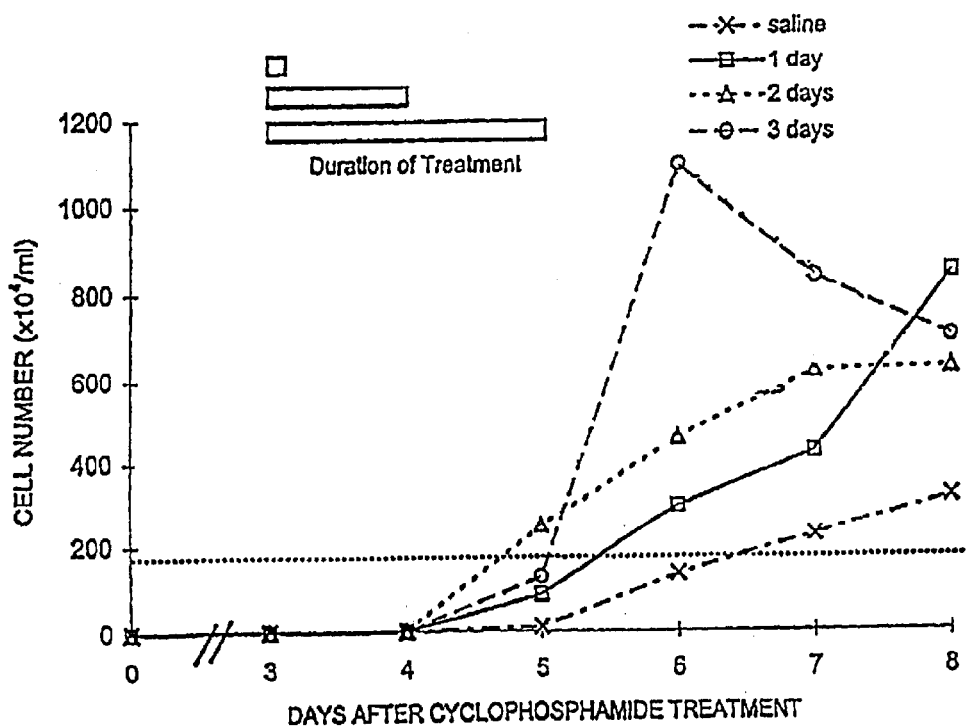
FIG. 6 is a graph depicting the effect of duration of PT-100 administration on absolute neutrophil count and rate of neutrophil recovery in cyclophosphamide-treated mice. PT-100 (5 µg/b.i.d.) was administered to cyclophosphamide-treated mice by gavage for the indicated length of time. The dashed horizontal line indicates the average absolute neutrophil count for mice not treated with cyclophosphamide.

Results shown in FIGS. 6 and 7 indicate that the PT-100 effect on the regeneration of neutrophils occurs early during treatment and continues until ANC between 1000 and 1400 are achieved. Repeated administrations affect the kinetics of neutrophil restoration during the early period but does not significantly alter the ANC reached after 3 days of administration.

In conclusion, PT-100 accelerates neutrophil reconstitution over that seen with saline even after a one day of treatment. An accelerated reconstitution of neutrophils is obtained with each additional day of treatment for up to three days. A fourth or fifth day of treatment did not significantly increase ANC or the kinetics of reconstitution.

Human Hematopoietic Cell Responses In Vitro

Hematopoiesis is sustained by a pool of hematopoietic stem cells (HSCs) that can self-renew and differentiate into hematopoietic progenitor cells (HPCs). HPCs are committed to specific lineages which can be identified based on their colony morphology when grown in semi-solid media in vitro, typically over a 2 week period. The colonies grown in the semi-solid colony assay are functionally defined as colony- or burst-forming units and include BFU-E and CFU-E (cells committed to the erythroid lineage), CFU-GM (cells committed to the granulocytic/monocytic lineage), BFU-MK and CFU-MK (cells committed to the megakaryocyte lineage) and CFU-GEMM (multipotent progenitors). Although the semi-solid colony assay is a valuable tool to identify factors, such as G-CSF, which affect terminal differentiation, it does not assess the proliferative potential or self renewing properties of the primitive hematopoietic progenitor cells (PHPCs) (Dexter, T. A. et al., *Acta Hemat.* 62:299–305 (1979); Chen, B. P. et al., *Immunological Reviews:* 15 7:41–51 (1997)).

An assay to evaluate the effect of a compound or of growth factors on PHPCs was first described by Dexter (Dexter T. M. et al, *J. Cell. Physiol.* 91:335–344 (1977)), and combines the Long-Term Culture (LTC) with the semi-solid colony assay. LTC is initiated over a pre-formed stromal cell layer which provides the necessary hematopoietic growth factors. It has been used extensively for the in vitro examination of murine and human hematopoiesis and to evaluate the ability of test compounds to generate LTC-ICs.

The effect of PT-100 on growth of human hematopoietic cells was examined in the 2 week CFU and the 4 and 5 week LTC assays using human bone marrow, apheresed peripheral blood or umbilical cord blood cells. PT-100 did not stimulate the generation of CFUs in the 2 week semi-solid assay, indicating that PT-100 does not affect the differentiation of committed progenitor cells into mature blood cells. It also suggests, that the mechanism and the cellular targets for PT-100 for the stimulation of neutrophil regeneration in vivo is different from that of G-CSF which has been shown to stimulate CFU formation in this assay. In the LTC assays, which test for effects on early progenitor cells, PT-100 significantly increased the growth of very early progenitor cells from all three cell sources. Moreover, the data suggest that the effect of PT-100 is on PHPCs as increases in LTC-ICs were observed at 4 weeks (FIG. 8) 5 weeks and 6 weeks (data not shown) in culture. At this time less primitive hematopoietic progenitor cells have undergone terminal differentiation and lost the ability to form colonies in semi-solid cultures.

For the LTC assays, CD34$^+$ cells were isolated by positive selection from human bone marrow cells, apheresed peripheral blood or umbilical cord blood using a MAC separation system. To establish a stromal feeder layer, human bone marrow cells were cultured in Myelocult long term culture medium for 2 weeks. One day prior to use, the adherent stromal cells were cultured overnight with indicated concentrations of PT-100 in LTC medium and irradiated. Isolated CD34$^+$ cells were overlaid onto the stromal cell layer and incubated for 30 days in the absence or presence of indicated amounts of PT-100. Medium and PT-100 was exchanged every three days thereafter. At the end of the culture period the culture was assayed for progenitor cells by plating in semi-solid medium (methylcellulose) supplemented with growth factors (Stem Cell Factor, GM-CSF, IL-3 and Erythropoietin).

The total number of myeloid, erythroid, blast forming and multilineage clonogeneic progenitors (colonies CFU-GM, CFU-E, BFU-E and CFU-GEMM, respectively) were determined after 14 days in methylcellulose culture.

Figure 8:
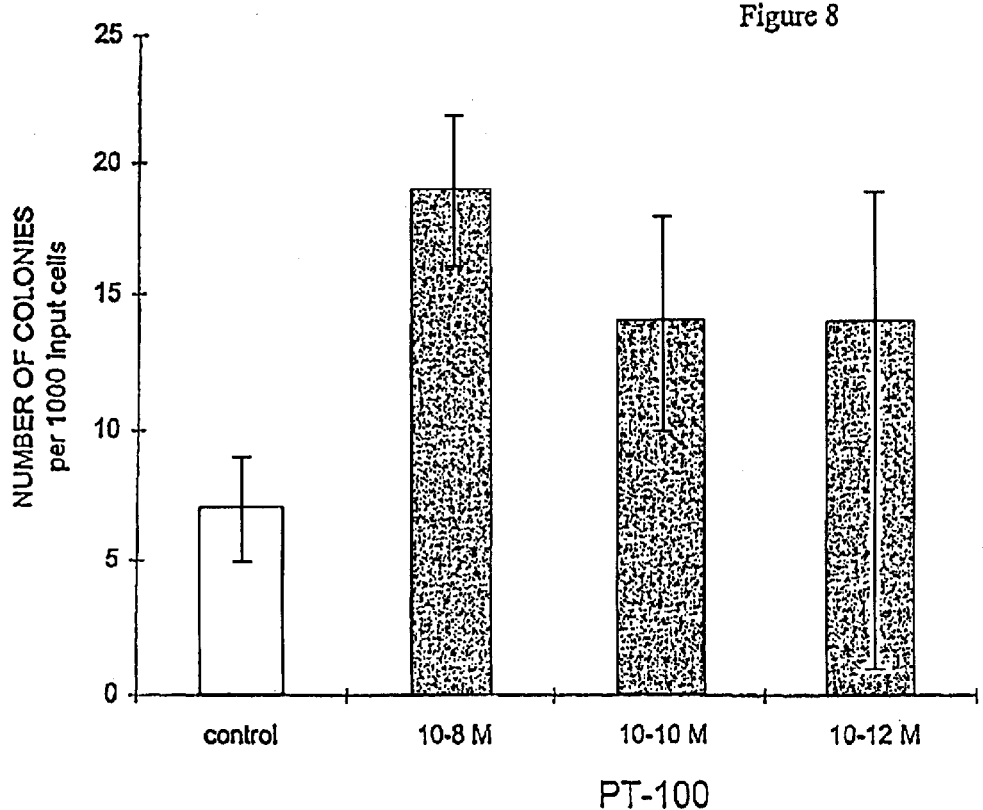
FIG. 8 is a graph depicting the colony formation ability of cells in response to PT-100 in a long-term culture (LTC) assay. Human bone marrow cells were incubated in LTC for 4 weeks in the absence or presence of indicated amounts of PT-100, followed by a 2 week culture in semi-solid medium.

Data showing in FIG. 8 for a human bone marrow culture indicate that during a 4 week LTC assay, PT-100 increased, in a dose dependent manner, the number of clonogeneic progenitors which are able to form colonies in semi-solid medium. This suggests that PT-100 stimulates growth of primitive hematopoietic progenitor cells.

In similar fashion CD34$^+$ cells purified from apheresed peripheral blood or umbilical cord blood were cultured on irradiated primary stromal cells for 30 days. As had been observed with bone marrow cells, PT-100 increased the number of 4 and 5 week LTC-ICs from peripheral and umbilical cord blood to very similar levels, indicating the PT-100 is able to stimulate primitive hematopoietic progenitor cell growth from these cell sources as well (data not shown).

PT-100 Does Not Stimulate Differentiation of Committed Progenitor Cells

Human bone marrow cells were enriched for CD34+ cells and 200 CD34+ cells per well were incubated in serum free x-vivo 15 medium (Biowhittaker) with or without the indicated concentrations of PT-100 for 4 hours at 37° C. The pre-incubated CD34+ cells were added to 0.9% methylcellulose in Iscove's MDM containing sub-optimal concentrations of recombinant human growth factors (5 ng/ml Stem Cell Factor, 1 ng/ml GM-CSF, 1 ng/ml IL-3, 0.3 units/ml Erythropoietin (Stem Cell Technologies Vancouver, BC). PT-100 was added to the medium at the same concentrations used for the pre-incubation. The methylcellulose mixture was plated in duplicate in 35 mm dishes and incubated for 14 days at 37° C. Progenitor colonies (CFU-E, CFU-GM, CFU-GEMM and BFU-E) were counted under an inverted microscope. PT-100 did not stimulate differentiation of these committed progenitor cells.

Stimulation of Hematopoiesis in the Spleen of Normal Mice

Figure 9:
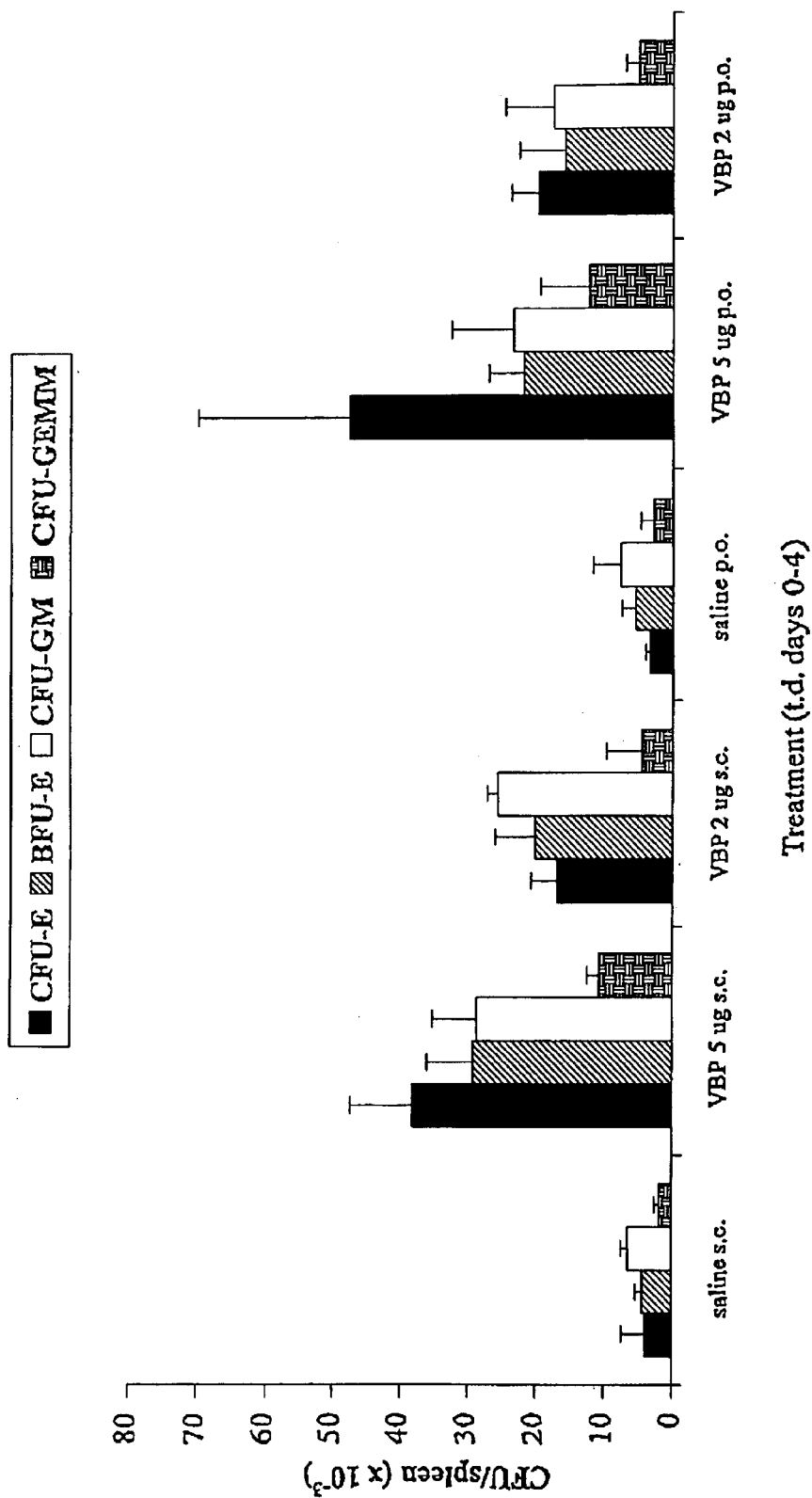
FIG. 9 is a graph showing that PT-100 stimulates hematopoiesis in the spleen of normal mice.

6–8 week old female BALB/c mice were administered either saline or PT-100 twice daily for 5 days at the indicated doses via either subcutaneous injection or oral gavage. On the sixth day the animals were sacrificed and their spleens were excised using sterile procedures. The spleens were disrupted to produce single cell suspensions which were subsequently treated with a solution of Tris ammonium chloride (pH 7.2) to lyse erythrocytes. The resulting splenocyte populations were in a hemocytometer and resuspended at $5 \times 10^6$ cells/mL in Iscove's Modified Eagles medium (IMDM) supplemented with 2% heat inactivated fetal calf serum. 0.3 mL of each splenocyte solution was added to 3 mL of Methocult™GF M3434 (Stem Cell Technologies, Vancouver, BC, Canada), a methylcellulose medium containing recombinant cytokines used for colony assays of murine progenitor cells. The medium was vigorously mixed and then 1.1 mL of the mixture was placed in duplicate onto sterile 35 mm diameter culture dishes, resulting in $5 \times 10^5$ splenocytes/plate. The plated cells were incubated at 37° C. under humidified conditions in 95% air/5% $CO_2$ for 7 days. CFU-E were enumerated as per the manufacturers specifications after 2 days, while BFU-E, CFU-GM and CFU-GEMM were enumerated after 7 days. For each mouse, the absolute CFU/spleen were calculated using the total splenocyte count determined in the hemocytometer. The data shown in FIG. 9 represents the mean ±SD CFU/spleen from 3 mice in each dosing group. PT-100 stimuated hematopoiesis for all progenitor colony types tested.

PT-100 Induces Production of G-CSF From Human Bone Marrow Stromal Cells

Figure 10:
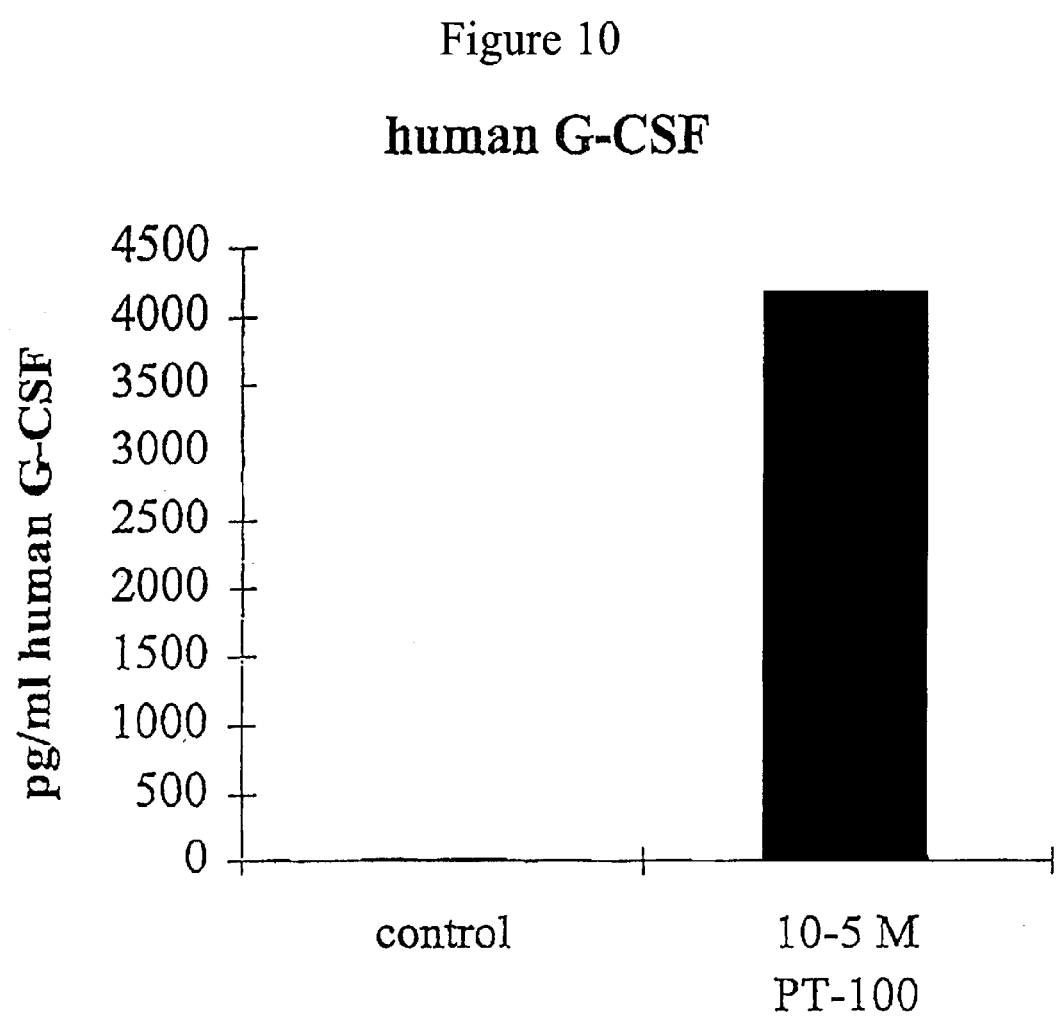
FIG. 10 is a graph showing that PT-100 stimulates production of G-CSF by human stromal cells.

Mononuclear cells were purified from bone marrow and cultured long-term culture medium, (Stem Cell Technologies, Inc., Vancouver, B.C.) for 2 weeks, with a single feeding of fresh medium after 1 week. The established stromal cells were removed by trypsin-EDTA digest and seeded into a 35 mm tissue culture plate at $10^6$ cells per well in 1 ml of medium containing $10^{-5}$ M PT-100 or medium alone as control. Culture media were collected on day 1. Supernatants were assayed for human G-CSF using a Quantikine high sensitivity immuno-assay kit (R+D Systems, Minneapolis, Minn.). FIG. 10 depicts the effect of PT-100 on the production of G-CSF by cultured human stomal cells. PT-100 stimulates production of G-CSF by such cells.

The manufacture of L-VAL-R-boroPro is described in a number of published procedures (Kelly, T. A., et al. *J. Am. Chem. Soc.* 1993. 115:12537–12638; Coutts, S. J., et al., *J. Med. Chem.* 1996. 39:2087–2094; Beak, P., et al., *Tetrahedon Letters*, 1989, 30:1197; Bean, F. R., et al., *J. Amer. Chem. Soc.* 1932. 54:4415). Pure isomers are preferred. See also U.S. Pat. Nos. 4,935,493 and 5,462,928, the disclosures of which are incorporated here by reference.

While the invention has been described with respect to certain embodiments, it should be appreciated that many modifications and changes may be made by those of ordinary skill in the art without departing from the spirit of the invention. It is intended that such modifications, changes, and equivalents fall within the scope of the following claims.

We claim:

1. A method for treating a subject to stimulate hematopoiesis of hematopoietic cells other than mature lymphocytes in the subject, comprising:

administering to a subject in need of such treatment an amount of an agent effective to increase the number of hematopoietic cells other than mature lymphocytes in the subject, wherein the agent is administered orally in an amount less than 1 mg/kg body weight per day and wherein the agent is a compound of Formula I:

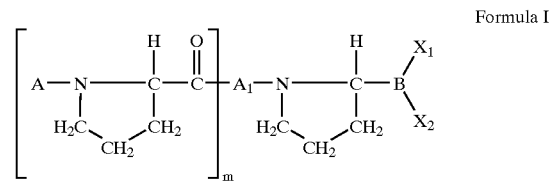

Formula I wherein m is an integer between 0 and 10, inclusive; A and $A_1$ are L-amino acid residues such that the A in each repeating bracketed unit can be the same or a different amino acid residue; the C bonded to B is in the L-configuration; the bonds between A and N, $A_1$ and C, and between $A_1$ and N are peptide bonds; and each $X_1$ and $X_2$ is, independently, a hydroxyl group or a group capable of being hydrolyzed to a hydroxyl group in aqueous solution at physiological pH.

2. The method of claim 1, wherein the subject has an abnormally low level of hematopoietic cells and wherein the agent is administered in an amount effective to restore levels of a hematopoietic cell-type to a preselected normal or protective level.

3. The method of claim 1, wherein the subject is administered at least two doses of the agent in an 18 hour period.

4. The method of claim 2, wherein the subject is neutropenic and wherein said amount is effective to restore a preselected normal or protective level of neutrophils.

5. The method of claim 2, wherein the subject has abnormally low levels of erythrocytes and wherein said amount is effective to restore a preselected normal or protective level of erythrocytes.

6. The method of claim 2, wherein the subject has abnormally low levels of platelets and wherein said amount is effective to restore a preselected normal or protective level of platelets.

7. A method for shortening the time that a subject has an abnormally low level of hematopoietic or mature blood cells resulting from treatment with a hematopoietic cell inhibitor, comprising:

administering to a subject in need of such treatment an agent in an amount effective to increase the number of hematopoietic cells or mature blood cells in the subject, wherein the administration of the agent is prior to or substantially simultaneous with administration of the hematopoietic cell inhibitor, wherein the agent is administered orally in an amount less than 1 mg/kg body weight per day and wherein the agent is a compound of Formula I:

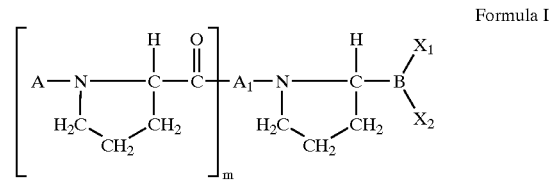

Formula I wherein m is an integer between 0 and 10, inclusive; A and $A_1$ are L-amino acid residues such that the A in each repeating bracketed unit can be the same or a different amino acid residue; the C bonded to B is in the L-configuration; the bonds between A and N, $A_1$ and C, and between $A_1$ and N are peptide bonds; and each $X_1$ and $X_2$ is, independently, a hydroxyl group or a group capable of being hydrolyzed to a hydroxyl group in aqueous solution at physiological pH.

8. The method of claim 7, wherein the administration of the hematopoietic cell inhibitor causes an abnormally low level of hematopoietic cells in the subject and wherein the agent is administered in an amount effective to restore levels of a hematopoietic cell-type to a preselected normal or protective level.

9. The method of claim 8, wherein the subject is administered at least two doses of the agent in an 18 hour period.

10. The method of claim 8, wherein the hematopoietic cell inhibitor reduces in the subject neutrophils and wherein the amount is effective to restore in the subject a preselected normal or protective level of neutrophils.

11. The method of claim 8, wherein the hematopoietic cell inhibitor reduces in the subject erythrocytes and wherein the amount is effective to restore in the subject a preselected normal or protective level of erythrocytes.

12. A method for treating a subject to increase the number of hematopoietic cells other than mature lymphocytes in the subject comprising:

administering to a subject in need of such treatment an amount of an agent effective to increase hematopoietic cells other than mature lymphocytes in the subject, wherein the agent is administered in a first regimen consisting of 2 doses or 3 doses in an 18 hour period, wherein the agent is administered orally in an amount less than 1 mg/kg body weight per day and wherein the agent is a compound of Formula I:

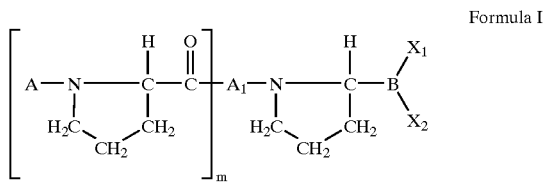

Formula I wherein m is an integer between 0 and 10, inclusive; A and $A_1$ are L-amino acid residues such that the A in each repeating bracketed unit can be the same or a different amino acid residue; the C bonded to B is in the L-configuration; the bonds between A and N, $A_1$ and C, and between $A_1$ and N are peptide bonds; and each $X_1$ and $X_2$ is, independently, a hydroxyl group or a group capable of being hydrolyzed to a hydroxyl group in aqueous solution at physiological pH.

13. The method of claim 1, 2, 3, 4, 5 or 6, wherein the agent is ValBoroPro.

14. The method of claim 8, wherein the hematopoietic cell inhibitor reduces in the subject platelets and wherein the amount is effective to restore in the subject a preselected normal or protective level of platelets.

15. The method of claim 7, 8, 9, 10, 11 or 14, wherein the agent is ValBoroPro.

16. The method of claim 12, wherein the agent is administered in a second regimen consisting of 2 doses or 3 doses in an 18 hours period, and wherein, the second regimen is separate in time from the first regimen.

17. The method of claim 16, wherein the agent is administered in a third regimen consisting of 2 doses or 3 doses in an 18 hours period, and wherein, the third regimen is separate in time from the first and second regimens.

18. The method of claim 17, wherein the agent is administered in a fourth regimen consisting of 2 doses or 3 doses in an 18 hours period, and wherein, the fourth regimen is separate in time from the first, second, and third regimens.

19. The method of claim 18, wherein the agent is administered in a fifth regimen consisting of 2 doses or 3 doses in an 18 hours period, and wherein, the fifth regimen is separate in time from the first, second, third and fourth regimens.

20. The method of claim 12, 16, 17, 18 or 19, wherein the subject has abnormally low neutrophils and, wherein said amount is effective to restore a preselected normal or protective level of neutrophils.

21. The method of claim 12, 16, 17, 18 or 19, wherein the agent is ValBoroPro.

* * * * *

UNITED STATES PATENT AND TRADEMARK OFFICE
CERTIFICATE OF CORRECTION

PATENT NO.     : 6,770,628 B2
DATED          : August 3, 2004
INVENTOR(S)    : Wallner et al.

It is certified that error appears in the above-identified patent and that said Letters Patent is hereby corrected as shown below:

<u>Title page</u>,
Item [62], Related U.S. Application Data, delete "Division" and insert
-- Continuation --;

<u>Column 20</u>,
Lines 20, 24, 28 and 32, delete "hours" and insert -- hour --.

Signed and Sealed this

Fourteenth Day of December, 2004

JON W. DUDAS
*Director of the United States Patent and Trademark Office*